(12) United States Patent
Bonnamy et al.

(10) Patent No.: US 11,273,112 B2
(45) Date of Patent: Mar. 15, 2022

(54) PROCESS FOR TREATING KERATIN FIBERS USING A HALOCHROMIC TRIARYLMETHANE DIRECT DYE, AN ALKALINE REVEALER AND THEN AN ACIDIC ERASER

(71) Applicant: L'OREAL, Paris (FR)

(72) Inventors: Arnaud Bonnamy, Saint-Ouen (FR); Frédéric Simonet, Saint-Ouen (FR); Maxime Pourret, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/955,027

(22) PCT Filed: Dec. 18, 2018

(86) PCT No.: PCT/EP2018/085413
§ 371 (c)(1),
(2) Date: Jun. 17, 2020

(87) PCT Pub. No.: WO2019/121628
PCT Pub. Date: Jun. 27, 2019

(65) Prior Publication Data
US 2020/0390674 A1    Dec. 17, 2020

(30) Foreign Application Priority Data
Dec. 21, 2017   (FR) ...................... 1762785

(51) Int. Cl.
*A61Q 5/10*    (2006.01)
*A61K 8/49*    (2006.01)
*A61K 8/46*    (2006.01)

(52) U.S. Cl.
CPC .............. *A61K 8/498* (2013.01); *A61K 8/466* (2013.01); *A61K 8/49* (2013.01); *A61Q 5/10* (2013.01); *A61K 2800/48* (2013.01)

(58) Field of Classification Search
CPC ........ A61Q 5/10; A61Q 5/065; A61K 8/4926; A61K 8/49; A61K 8/342; A61K 8/347; A61K 8/498; A61K 8/466; A61K 2800/48; A61K 2800/432
USPC ........................................... 8/405
See application file for complete search history.

(56) References Cited

U.S. PATENT DOCUMENTS

| | | |
|---|---|---|
| 2,798,053 A | 7/1957 | Brown |
| 2,923,692 A | 2/1960 | Ackerman et al. |
| 3,915,921 A | 10/1975 | Schlatzer, Jr. |
| 4,128,508 A | 12/1978 | Munden |
| 4,131,576 A | 12/1978 | Iovine et al. |
| 4,150,106 A | 4/1979 | Assal et al. |
| 4,237,243 A | 12/1980 | Quack et al. |
| 4,509,949 A | 4/1985 | Huang et al. |
| 5,089,578 A | 2/1992 | Valint et al. |
| 5,474,578 A * | 12/1995 | Chan ...................... A61K 8/411 8/405 |
| 6,822,039 B1 | 11/2004 | Monfreux-Gaillard et al. |
| 2004/0143910 A1 | 7/2004 | Said |
| 2012/0141398 A1 | 6/2012 | Chuang |
| 2017/0258695 A1 * | 9/2017 | Consoli ................... A61K 8/55 |

FOREIGN PATENT DOCUMENTS

| | | | |
|---|---|---|---|
| CN | 1077884 A | 11/1993 | |
| DE | 102008057018 A1 * | 7/2010 | ............... A61Q 5/10 |
| EP | 0173109 A2 | 3/1986 | |
| EP | 0503853 A2 | 9/1992 | |
| EP | 0750899 A2 | 1/1997 | |
| EP | 2926868 A1 | 10/2015 | |
| FR | 1441822 A | 6/1966 | |
| FR | 2356431 A1 | 1/1978 | |
| FR | 2416723 A1 | 9/1979 | |
| FR | 2456518 A | 12/1980 | |
| FR | 2902322 A1 | 12/2007 | |
| GB | 2050829 A | 1/1981 | |
| WO | 98/44012 A1 | 10/1998 | |
| WO | 00/31154 A1 | 6/2000 | |
| WO | 00/68282 A1 | 11/2000 | |
| WO | WO 2010054981 A2 * | 5/2010 | ............... A61Q 5/10 |

OTHER PUBLICATIONS

STIC Search Report dated Apr. 23, 2021.*
International Search Report and Written Opinion for counterpart Application No. PCT/EP2018/085413, dated Mar. 26, 2019.
Bagda, E., "The relation between surface tension and solubility parameter in liquids," Farbe Lack, 84, 1978, p. 212.
Barton, "Handbook of Solubility Parameters and Other Cohesion Parameters," CRC Press, Second Edition, 1991, pp. 95-121 and 176-185.
Fonnum, G., et al., "Associative Thickeners. Part I: Synthesis, Rheology and Aggregation Behavior," Colloid Polym. Sci., 271, (1993) pp. 380-389.

(Continued)

*Primary Examiner* — Eisa B Elhilo
(74) *Attorney, Agent, or Firm* — The Marbury Law Group, PLLC

(57) ABSTRACT

The present invention relates to a process for treating keratin fibers, especially human keratin fibers such as the hair, using i) at least one triarylmethane or sulfonophthalein direct dye of formula (I) or (I') as defined below, ii) an alkaline revealer, iii) an eraser at acidic pH. A subject of the invention is also a composition comprising at least one triarylmethane direct dye of formula (I) or (I') as defined below and at least one thickener and/or at least one hydrotropic solvent, and a multi-compartment kit comprising i), ii) and iii) in three separate compartments. The present invention makes it possible in particular to obtain keratin fiber coloring with intense and persistent tints which can be modified, erased and reformed several times without any loss of color.

20 Claims, No Drawings

(56) References Cited

OTHER PUBLICATIONS

Morishima, Yotaro, "Self-Assembling Amphiphilic Polyelectrolytes and their Nanostructures," Chinese Journal of Polymer Science, vol. 18, No. 40, (2000), pp. 323-336.

Noda, Tetsuya, et al., "Micelle Formation of Random Copolymers of Sodium 2-(Acrylamido)-2-Methylpropanesulphonate and a Nonionic Surfactant Macromonomer in Water as Studied by Fluorescence and Dynamic Light Scattering," Macromolecules 2000, 33, pp. 3694-3704.

Noda, Tetsuya et al., "Solution Properties of Micelle Networks Formed by Nonionic Surfactant Moieties Covalently Bound to a Polyelectrolyte: Salt Effects on Rheological Behavior," Langmuir 2000, 16, pp. 5324-5332.

Noda, Tetsuya, et al., "Stimuli-Responsive Amphiphilic Copolymers of Sodium 2-(Acrylamido)-2-Methylpropanesulphonate and Associative Macromonomers," Polym. Preprint, Div. Polym. Chem. 1999, 40(2), pp. 220-221.

Zviak, Charles, "Science Des Traitements Capillaires," [Hair Treatment Science], published by Masson, 1988, pp. 214-279.

* cited by examiner

PROCESS FOR TREATING KERATIN FIBERS USING A HALOCHROMIC TRIARYLMETHANE DIRECT DYE, AN ALKALINE REVEALER AND THEN AN ACIDIC ERASER

CROSS REFERENCE TO RELATED APPLICATION

This is a national stage application of PCT/EP2018/085413, filed internationally on Dec. 18, 2018, which claims priority to French Application No. 1762785, filed on Dec. 21, 2017, both of which are incorporated by reference herein in their entireties.

The present invention relates to a process for treating keratin fibers, especially human keratin fibers such as the hair, using i) at least one triarylmethane or sulfonophthalein direct dye of formula (I) or (I') as defined below, then ii) an alkaline revealer, and then iii) an eraser at acidic pH. A subject of the invention is also a composition comprising at least one triarylmethane direct dye of formula (I) or (I') as defined below and at least one thickener and/or at least one hydrotropic solvent, and a multi-compartment kit comprising i), ii) and iii) in three separate compartments.

It is known practice to dye keratin fibers, and in particular human keratin fibers such as the hair, with dye compositions containing oxidation dye precursors, which are generally known as oxidation bases, such as ortho- or para-phenylenediamines, ortho- or para-aminophenols and heterocyclic compounds such as diaminopyrazole derivatives. These oxidation bases are colorless or weakly colored compounds which, when combined with oxidizing products, can give rise to colored compounds via a process of oxidative condensation.

It is also known that the shades obtained with these oxidation bases may be varied by combining them with couplers or color modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

The "permanent" coloring obtained by means of these oxidation dyes should moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow gray hair to be covered and, finally, they should be as unselective as possible, i.e. they should produce the smallest possible differences in color along the same keratin fiber, which in general is differently sensitized (i.e. damaged) between its end and its root.

It is also known practice to dye keratin fibers, and in particular human keratin fibers such as the hair, with dye compositions containing direct dyes. These dyes are colored and coloring molecules that have affinity for keratin fibers, They are applied to the keratin fibers for a time necessary to obtain the desired coloring, and are then rinsed out.

The conventional dyes that are used are, in particular, dyes of the nitrobenzene, anthraquinone, nitropyridine, azo, cationic azo, xanthene, acridine, azine, triarylmethane type, or natural dyes.

The colorings obtained are temporary or semi-permanent, since the nature of the interactions that bind the direct dyes to the keratin fiber and their desorption from the surface and/or the core of the fiber are responsible for their weak dyeing power and their poor persistence with respect to washing, inclement weather or perspiration. These direct dyes are also generally light-sensitive due to the low resistance of the chromophore to photochemical attack, and lead to fading of the coloring of the hair over time.

It is also sought by users to be able to dye keratin fibers as they wish by making the color of the fibers appear with a revealer (switch on) and then to erase or switch off the color with a color eraser (switch off) and, if need be, to repeat these switch-on-switch-off cycles, with very little loss of color after a switch-on cycle repetition. It is also sought to be able, even after several shampoo washes, to switch on or switch off this color without damaging the keratin fibers.

The use, for the dyeing of keratin fibers, of particular halochromic compounds is known in the prior art. For example, mention may be made of US 2012/0141398, which describes a process for dyeing the hair with a dye of triarylmethane type (Erioglaucine A). However, the prior art processes do not describe successive steps of "switch on-switch off-switch on-switch off" dyeing. In addition, the dyes are not always sufficiently persistent, and/or there is a decrease in the color properties of the color revealed in terms of color build-up, intensity, chromaticity, persistence especially with respect to successive shampoo washing, and/or selectivity of the color between the root and the end. Furthermore, in pH ranges close to neutrality, these dyes are not always switchable for "switch off-switch on" or "switch on-switch off" changes. Another problem encountered is that of rapid and sharp revealing or erasure of the color without any residual color remaining after the "switch off" color erasure step. Finally, there is a problem of diffusion when it is desired to perform artistic dyeing by revealing only part of the color or erasing only part of the color. The coloring result or the erasure result is not always satisfactory, especially when a stencil is used, due to the diffusion of the erasure or revealing on the keratin fibers (running). In addition, a coloring system that can change color "switch on"-"switch off" with a "switch on" that is in natural colors known as fundamental colors, such as chestnuts, browns or even blacks, is sought.

FR1441822 discloses a process for preparing doll hair consisting of preparing a dyeing material containing a coloured indicator sensitive to pH and able to change colour in response to a pH change and applying this material to the doll hair. The doll hair is made of synthetic fibers such as cellulose acetate.

Thus, the aim of the invention is to provide keratin fiber colorings with intense colors, and a good color build-up which can switch as a function of the pH ideally close to neutrality, even after several cycles, with a rapid and sharp effect of the "switch off-switch on" color change, with structured effects (geometrical, graphic, etc. effect), without any color transfer from one lock to another (e.g. possibility on a braid comprising three dyes of different colors of there being no color diffusion from one lock to another even after several pH revealing cycles), and which can allow revealing or erasure of the color without running, and avoid denaturing of the keratin fibers. Another aim is to be able to obtain coloring in fundamental colors that can be erased or change color sharply, visibly and rapidly.

This aim is achieved with the present invention, one subject of which is a process for treating keratin fibers, especially human keratin fibers such as the hair, involving:
i) a step of applying a composition (A) comprising one or more triarylmethane or sulfonophthalein compounds of formula (I) or (I'), and also mineral or organic base salts thereof, optical, geometrical and tautomeric isomers thereof, and also solvates thereof such as hydrates:

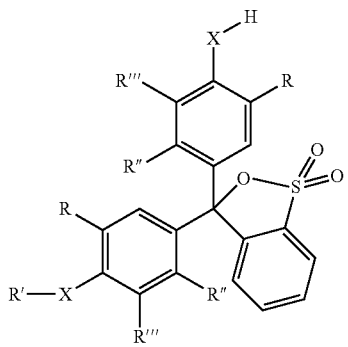
(I)

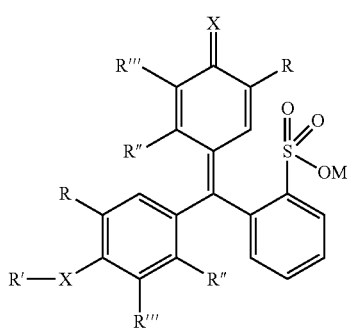
(I')

in which formulae (I) and (I'):
R represents a hydrogen atom, a halogen atom such as chlorine or bromine, or a group chosen from $(C_1\text{-}C_6)$alkyl and $(C_1\text{-}C_6)$alkoxy;
R' represent a hydrogen atom or $(C_1\text{-}C_6)$alkyl or a benzyl group;
R'' represents a hydrogen atom or a $(C_1\text{-}C_6)$alkyl or $(C_1\text{-}C_6)$alkoxy group;
R''' represents a hydrogen atom, a halogen atom such as chlorine or bromine, or a group chosen from hydroxyl, $(C_1\text{-}C_4)$alkyl, $(C_1\text{-}C_6)$alkoxy and carboxyl;
X represents a heteroatom such as O, S and NR', preferably O; and
M represents a hydrogen atom, an alkali metal, an alkaline-earth metal or ammonium;

and then:
when composition (A) comprises one or more compounds of formula (I), the application of composition (A) is followed ii) by a revealing ("switch on") step which consists in applying to said fibers a composition (B) at basic pH; followed iii) by a step of switching off or erasing the color ("switch off") which consists in applying to said fibers a composition (C) at acidic pH; and when composition (A) comprises one or more compounds of formula (I'), the application of composition (A) is followed iii) by a step of switching off the color which consists in applying to said fibers a composition (C) at acidic pH, followed ii) by a revealing step which consists in applying to said fibers a composition (B) at basic pH;

it being understood that steps ii) and iii) may be repeated several times.

Another subject of the invention is a composition $(A_1)$ comprising a) one or more triarylmethane or sulfonophthalein compounds of formulae (I) and/or (I') as defined previously and optionally b) one or more thickeners, in particular polymeric thickeners, and/or one or more hydrotropic solvents, in particular aromatic hydrotropic solvents.

Another subject of the invention is a multi-compartment kit which comprises, i) in a first compartment: the triarylmethane or sulfonophthalein compounds of formula (I) or (I') as defined previously, ii) in a second compartment: a composition (B) at basic pH; and iii) in a third compartment: a composition (C) at acidic pH.

i) The Dyes (I) or (I')

The keratin fiber treatment process of the invention involves in the first step a step of applying a composition (A) comprising one or more compounds of formula (I) or (I') as defined previously, or a step of applying $(A_1)$ as defined previously.

Preferably, the triarylmethane or sulfonophthalein compounds of formula (I) or (I') are dyes which have a color change zone at a pH inclusively between 4.5 and 8.

In the context of the present invention, the term "alkyl radical" means a linear or branched, saturated hydrocarbon-based radical comprising from 1 to 6 carbon atoms, preferably comprising between 1 and 4 carbon atoms, for example methyl, ethyl, n-propyl, isopropyl, n-butyl or tert-butyl.

An alkoxy radical is a radical alk-O— with the alkyl radical being as defined previously.

A carboxyl radical represents a carboxylic acid group —O(O)—OH.

As examples of compounds of formula (I) or (I'), mention may be made of the following compounds:

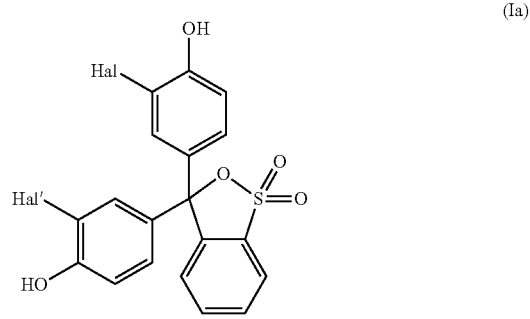
(Ia)

in which formula (Ia) Hal and Hal', which may be identical or different, represent a halogen atom such as chlorine or bromine, in particular chlorine.

-continued

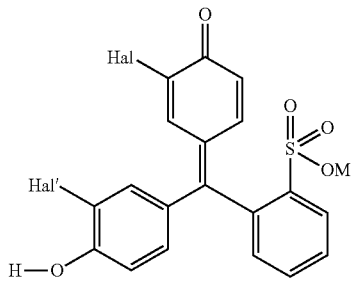
(I'a)

in which formula (I'a):
Hal and Hal', which
may be identical or different, represent a
halogen atom such as chlorine or bromine,
in particular chlorine; and
M is as defined previously, preferably
an alkali metal such as sodium or a
hydrogen atom, preferentially an
alkali metal such as sodium;

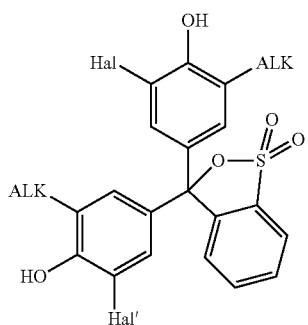
(Ib)

in which formula (Ib):
Hal and Hal', which
may be identical or different, represent a
halogen atom such as chlorine or bromine,
in particular bromine; and
ALK represents a $(C_1$-$C_6)$alkyl group,
which is preferably linear, in
particular methyl;

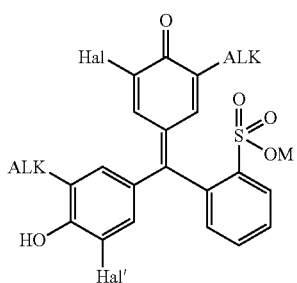
(I'b)

in which formula (I'b):
Hal and Hal', which
may be identical or different, represent a
halogen atom such as chlorine or bromine,
in particular bromine;
ALK represents a $(C_1$-$C_6)$alkyl group,
which is preferably linear, in
particular methyl; and
M is as defined previously, preferably
an alkali metal such as sodium or a
hydrogen atom, preferentially an
alkali metal such as sodium;

-continued

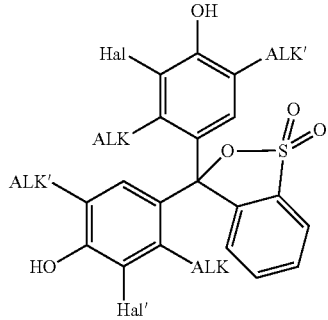
(Ic)

in which formula (Ic):
Hal and Hal', which may be identical
or different, represent a halogen
atom such as chlorine or bromine, in
particular bromine;
ALK represents a $(C_1$-$C_6)$alkyl group,
which is preferably linear, in
particular methyl; and
ALK' represents a $(C_1$-$C_6)$alkyl group,
which is preferably branched, such
as isopropyl;

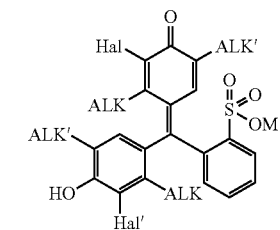
(I'c)

in which formula (I'c):
Hal and Hal', which may be identical
or different, represent a halogen
atom such as chlorine or bromine, in
particular bromine;
ALK represents a $(C_1$-$C_6)$alkyl group,
which is preferably linear, in
particular methyl;
ALK' represents a $(C_1$-$C_6)$alkyl group,
which is preferably branched, such
as isopropyl; and
M is as defined previously, preferably
an alkali metal such as sodium or a
hydrogen atom, preferentially an
alkali metal such as sodium;

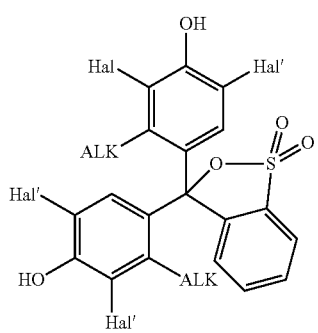

in which formula (Id):
Hal and Hal', which
may be identical or different, represent a
halogen atom such as chlorine or bromine,
in particular bromine; and
ALK represents a $(C_1-C_6)$alkyl group,
which is preferably linear, in
particular methyl;

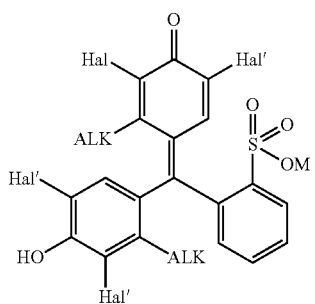

in which formula (I'd):
Hal and Hal', which may be identical
or different, represent a halogen
atom such as chlorine or bromine, in
particular bromine;
ALK represents a $(C_1-C_6)$alkyl group,
which is preferably linear, in
particular methyl; and
M is as defined previously, preferably
an alkali metal such as sodium or a
hydrogen atom, preferentially an
alkali metal such as sodium;

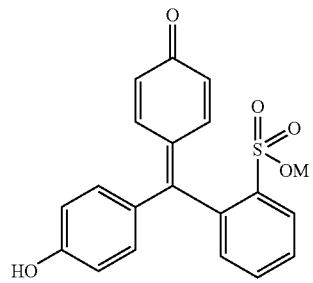

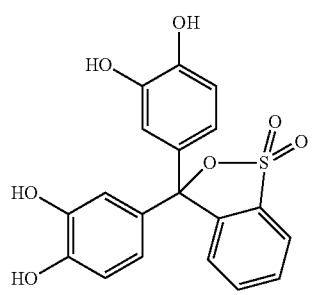

in which formula (I'e)
M is as defined previously, preferably
an alkali metal such as sodium or a
hydrogen atom;

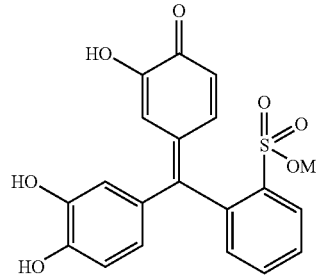

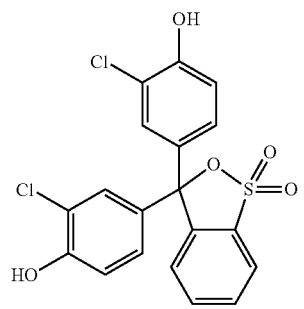

in which formula (I'f)
M is as defined previously, preferably
an alkali metal such as sodium or a
hydrogen atom;

and also the alkali metal or alkaline-earth metal salts thereof.

In particular, the compound(s) of formula (I) or (I') represent a compound of formula (Ia), (I'a), (Ib) and (I'b), (Ic), (I'c), (Ie) or (I'e).

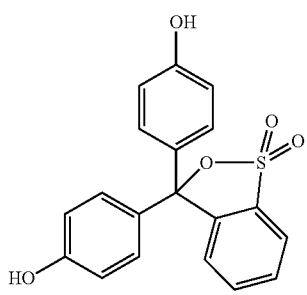

Chlorophenol Red (1')

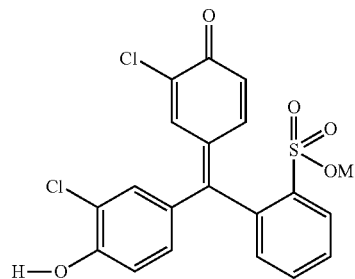

in which M is as defined previously, preferably
H or an alkali metal such as sodium, more preferentially sodium;
Chlorophenol Red (2)

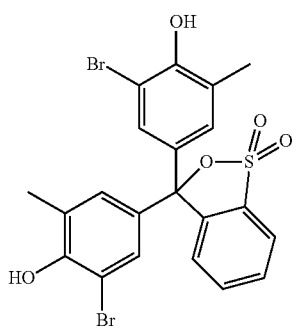

Bromocresol Purple (2')

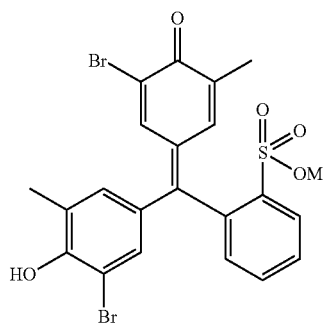

in which M is as defined previously, preferably
H or an alkali metal such as sodium;
Bromocresol Purple (3)

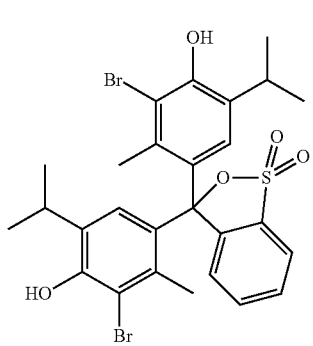

(3')

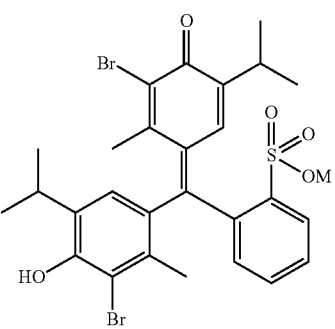

in which M is as defined previously, preferably
H or an alkali metal such as sodium;
Bromothymol Blue (4)

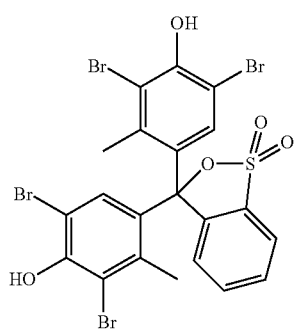

(4')

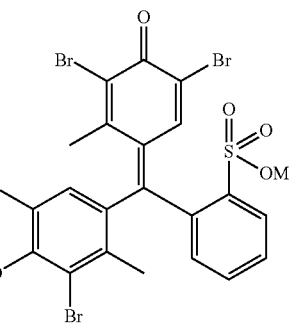

in which M is as defined previously, preferably
H or an alkali metal such as sodium;
Bromocresol Green (5)

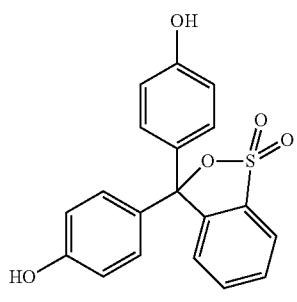

(5')

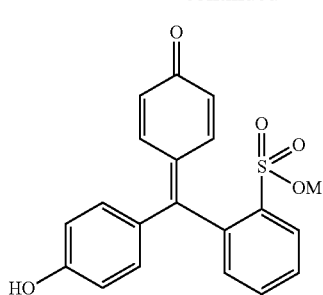

in which M is as defined previously, preferably H or an alkali metal such as sodium;
Phenol Red (6)

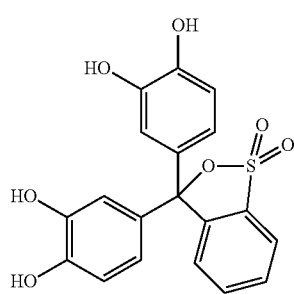

(6')

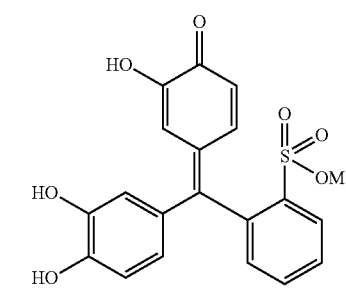

in which M is as defined previously, preferably H or an alkali metal such as sodium.
Catechol Violet In particular, the compound(s) of formula (I) or (I') represent a compound of formula (1), (1'), (2), (2'), (3), (3'), (5) or (5').

According to a particular embodiment of the invention, the compounds of formulae (I) and (I') as defined previously preferentially represent from 0.001% to 10% by weight and preferably from 0.005% to 5% by weight relative to the total weight of composition (A).

According to a particular embodiment of the invention, composition $(A_1)$ comprises one or more compounds of formulae (I) and/or (I') as defined previously in an amount of between 0.001% to 10% by weight, preferably between 0.005% to 5% by weight relative to the total weight of composition $(A_1)$.

In general, the organic or mineral base addition salts of the compounds of formula (I) in which the sulfonate ring is closed and the dyes corresponding to the compounds of formula (I') in which the sulfonate ring is open, which may be used in the context of the invention, are especially chosen from the base addition salts chosen from the alkaline agents as defined below, in particular chosen from sodium hydroxide, potassium hydroxide, ammonia and alkanolamines.

Optional Dyes:

Compositions (A) and $(A_1)$ as defined previously may also comprise one or more direct dyes other than the compounds of formulae (I) and/or (I') as defined previously, which may be chosen especially from nitrobenzene dyes, azo direct dyes, methine direct dyes and natural dyes. These direct dyes may be of nonionic, anionic or cationic nature. These dyes may be halochromic.

Preferably, the process of the invention uses one or more halochromic additional dyes other than the triarylmethanes of formula (I) or (I') as defined previously, preferably of formula (II) or (II') as defined below.

Preferably, compositions (A) and $(A_1)$ as defined previously also comprise one or more halochromic additional dyes other than the triarylmethanes of formula (I) or (I') as defined previously. More preferentially, the halochromic additional dye(s) other than triarylmethanes are chosen from the fluorescein compounds of formulae (II) and (II'), and also the mineral or organic base salt(s) thereof, the optical, geometrical and tautomeric isomer(s) thereof, and also the solvate(s) thereof such as hydrates:

(II)

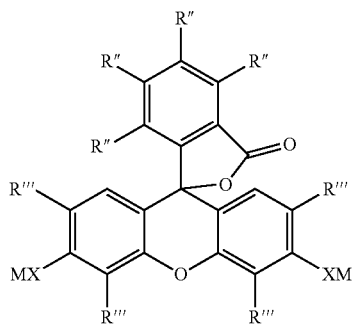

(II')

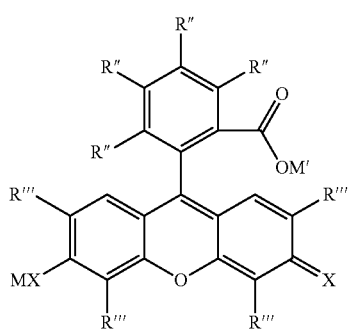

in which formulae (II) and (II'):

R" represents a hydrogen atom, a halogen atom such as chlorine or bromine, or a group chosen from i) ($C_1$-$C_6$)alkyl which is optionally substituted, in particular with one or more halogen atoms such as bromine, ii) optionally substituted ($C_1$-$C_6$)alkoxy, iii) $R_a$—C(X)—, iv) $R_a$—C(X)—X—, v) $R_a$—X—C(X)—, and vi) iso(thio)cyanate with $R_a$ representing a hydrogen atom, a heterocyclic group such as N-succinimide or a ($C_1$-$C_4$) alkyl group optionally substituted with one or more halogen atoms such as bromine or iodine, or with one or more carboxyl groups; preferably, R" represents a hydrogen atom or a halogen atom such as chlorine or bromine;

R'" represents i) a hydrogen atom, ii) a halogen atom such as chlorine, bromine or iodine or iii) a group chosen from ($C_1$-$C_6$)alkyl which is optionally substituted, especially with one or more groups from among: a) hydroxyl, b) (di)($C_1$-$C_4$)(alkyl)amino, c) (di)carboxy ($C_1$-$C_4$)alkylamino, and iv) ($C_1$-$C_6$)alkoxy; preferably a hydrogen atom or a halogen atom such as chlorine, bromine or iodine;

X represents a heteroatom such as O, S or NR' with R' representing a hydrogen atom or a ($C_1$-$C_6$)alkyl group, preferably O; and M represents a hydrogen atom, an alkali metal or alkaline-earth metal, an ammonium group or a ($C_1$-$C_6$)alkyl (thio)carbonyl group, in particular ($C_1$-$C_4$)alkylcarbonyl such as acyl; and M' represents a hydrogen atom, an alkali metal, an alkaline-earth metal or an ammonium group, preferably hydrogen or an alkali metal such as sodium.

Preferably, the fluorescein compounds of formula (II) or (II') are dyes which have a color change zone at a pH inclusively between 4.5 and 8.

As examples of compounds of formula (II) or (II'), mention may be made of the following compounds:

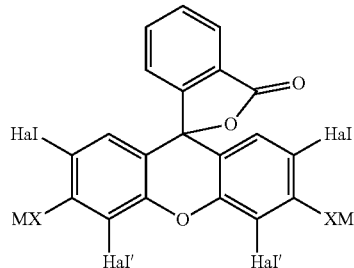

(IIa)

- in which formula (IIa) HaI and HaI', which may be identical or different, represent a halogen atom such as chlorine, bromine or iodine; in particular, HaI and HaI' are identical and preferably X is as defined previously, preferably represents an oxygen atom; and M is as defined previously, preferably an alkali metal or a hydrogen atom, preferentially an alkali metal such as sodium;

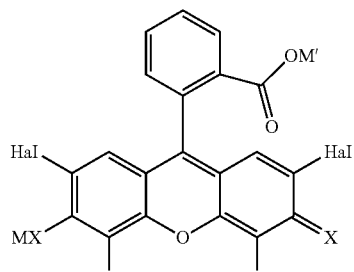

(II'a)

in which formula (II'a):
- HaI and HaI', which may be identical or different, represent a halogen atom such as chlorine, bromine or iodine; in particular, HaI and HaI' are identical and preferably represent a halogen atom such as bromine or iodine;

X is as defined previously, preferably represents an oxygen atom;

M is as defined previously, preferably an alkali metal or a hydrogen atom, preferentially an alkali metal such as sodium; and M' is as defined previously, in particular represents a hydrogen atom or an alkali metal such as sodium;

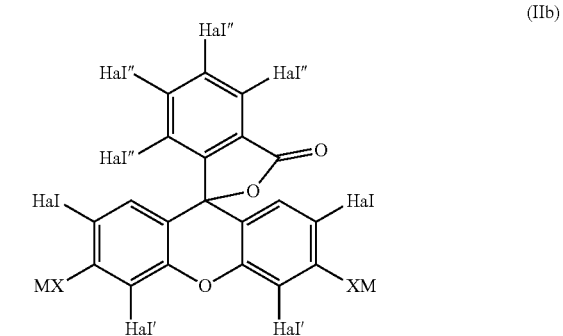

(IIb)

in which formula (IIb):
- HaI and HaI', which may be identical or different, represent a halogen atom such as chlorine or bromine; in particular, HaI and HaI' are identical and preferably represent a halogen atom such as bromine;
- HaI'' represents a halogen atom such as chlorine;

X is as defined previously, preferably represents an oxygen atom; and

M is as defined previously, preferably an alkali metal such as sodium or a hydrogen atom, preferentially an alkali metal such as sodium;

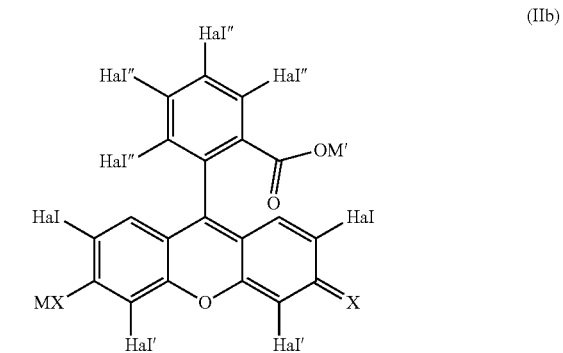

(II'b)

in which formula (II'b):
- HaI and HaI', which may be identical or different, represent a halogen atom such as chlorine or bromine; in particular, HaI and HaI' are identical and preferably represent a halogen atom such as bromine;
- HaI'' represents a halogen atom such as chlorine;

X is as defined previously, preferably represents an oxygen atom;

M is as defined previously, preferably an alkali metal such as sodium or a hydrogen atom, preferentially an alkali metal such as sodium; and M' is as defined previously, in particular represents a hydrogen atom or an alkali metal such as sodium;

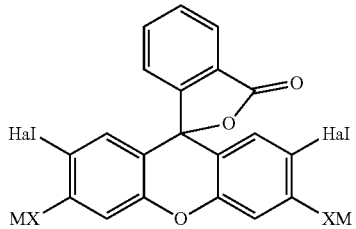

(IIc)

in which formula (IIc):
- Hal represents a halogen atom such as chlorine, bromine or iodine; in particular, Hal represents a halogen atom such as chlorine;
- X is as defined previously, preferably represents an oxygen atom;

and

M is as defined previously, preferably a $(C_1$-$C_4)$alkylcarbonyl group such as acyl;

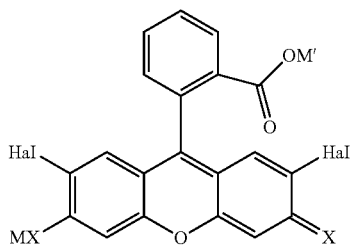

(II'c)

in which formula (II'c):
- Hal represents a halogen atom such as chlorine, bromine or iodine; in particular, Hal represents a halogen atom such as chlorine;
- X is as defined previously, preferably represents an oxygen atom;

M is as defined previously, preferably a $(C_1$-$C_4)$alkylcarbonyl group such as acyl; and M' is as defined previously, in particular represents a hydrogen atom or an alkali metal such as sodium;

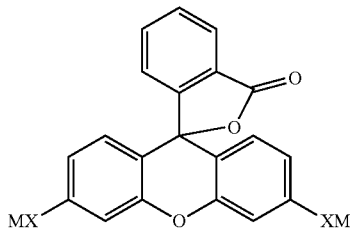

(IId)

in which formula (IId):
X is as defined previously, preferably represents an oxygen atom; and
M is as defined previously, preferably a hydrogen atom or an alkali metal such as sodium or a $(C_1$-$C_4)$alkylcarbonyl group such as methylcarbonyl; preferably hydrogen;

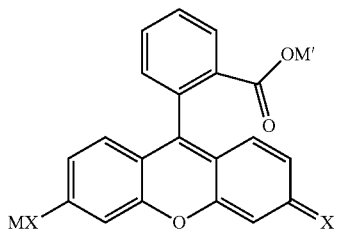

(II'd)

in which formula (II'd):
X is as defined previously, preferably represents an oxygen atom;
M is as defined previously, preferably a hydrogen atom or an alkali metal such as sodium or a $(C_1$-$C_4)$alkylcarbonyl group such as methylcarbonyl; preferably hydrogen;

and

M' is as defined previously, in particular represents a hydrogen atom or an alkali metal such as sodium, preferably hydrogen;

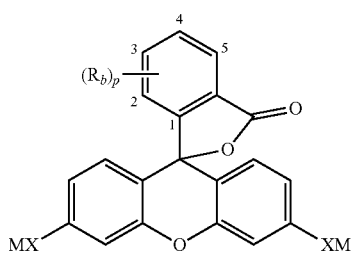

in which formula (IIe):
- $R_b$ represents a group from among:
  i) optionally substituted ($C_1$-$C_4$)alkyl, ii) isothiocyanate, iii) $R_a$-O-C(O)- or iv) $R_a$-C(O)-N(R')- with $R_a$ as defined previously; in particular, R' represents a hydrogen atom and $R_a$ represents a hydrogen atom or a ($C_1$-$C_4$)alkyl group optionally substituted with one or more halogen atoms such as bromine or iodine; preferably, $R_b$ represents a ($C_1$-$C_4$)alkyl group optionally substituted with one or more halogen atoms such as bromine or iodine;

X is as defined previously, preferably represents an oxygen atom;
p represents an integer between 1 and 5 inclusive; preferably, p is equal to 1; in particular, $R_b$ is in position 3 or 4 of the phenyl group; and
M is as defined previously, preferably a hydrogen atom or an alkali metal such as sodium, preferably hydrogen;

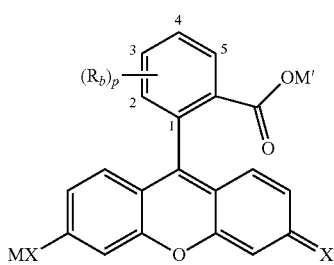

in which formula (II'e):
- $R_b$ represents a group from among:
  i) optionally substituted ($C_1$-$C_4$)alkyl, ii) isothiocyanate, iii) $R_a$-O-C(O)- or iv) $R_a$-C(O)-N(R')- with $R_a$ as defined previously; in particular, R' represents a hydrogen atom and $R_a$ represents a hydrogen atom or a ($C_1$-$C_4$)alkyl group optionally substituted with one or more halogen atoms such as bromine or iodine; preferably, $R_b$ represents a ($C_1$-$C_4$)alkyl optionally substituted with one or more halogen atoms such as bromine or iodine;

X is as defined previously, preferably represents an oxygen atom;
p represents an integer between 1 and 5 inclusive; preferably, p is equal to 1; in particular, $R_b$ is in position 3 or 4 of the phenyl group;

M is as defined previously, preferably a hydrogen atom or an alkali metal such as sodium, preferably hydrogen; and
M' is as defined previously, in particular represents a hydrogen atom or an alkali metal such as sodium, preferably hydrogen;

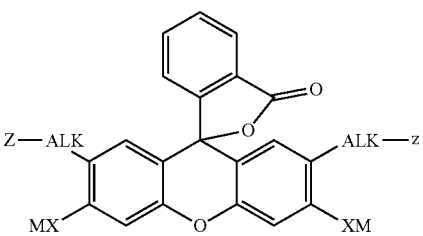

in which formula (IIf):
- ALK represents a ($C_1$-$C_4$)alkylene group;
- Z represents a group $NR_cR_d$ with Rc and Rd, which may be identical or different, representing a hydrogen atom or a ($C_1$-$C_4$)alkyl group optionally substituted with one or more carboxyl groups;

X is as defined previously, preferably represents an oxygen atom; and
M is as defined previously, preferably an alkali metal or a hydrogen atom, preferentially an alkali metal such as sodium;

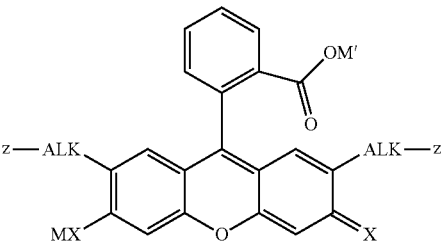

in which formula (II'f):
- ALK, z, X and M are as defined for (IIf)
- M' is as defined previously, in particular represents a hydrogen atom or an alkali metal such as sodium.

As examples of compounds of formula (II) or (II'), mention may be made of the compounds of formulae (IIa) to (II'f), and also the alkali metal or alkaline-earth metal salts thereof. In particular, the compound(s) of formula (II) or (II') represent a compound of formula (IIa), (II'a), (IIc), (II'c), (IId), (II'd), (IIe) or (IIe').

As examples of compounds of formula (II) or (II'), mention may be made of the following compounds:

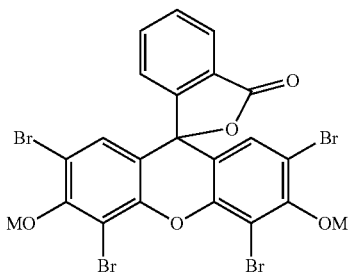

in which M is as defined previously, preferably represents a hydrogen atom or an alkali metal such as sodium;
Eosin

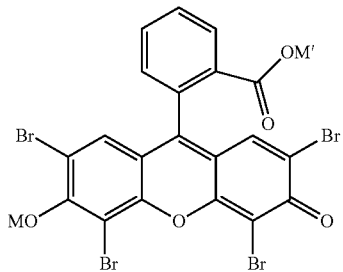

in which M and M' are as defined previously, preferably represent a hydrogen atom or an alkali metal such as sodium;
Eosin

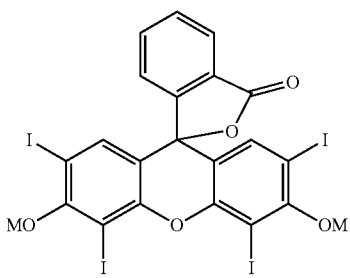

in which M is as defined previously, preferably represents a hydrogen atom or an alkali metal such as sodium;
Erythrosin

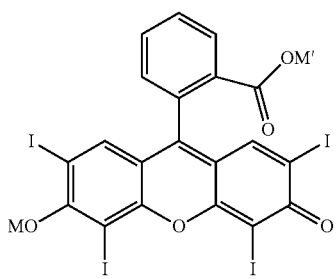

in which M and M' are as defined previously, preferably represent a hydrogen atom or an alkali metal such as sodium;
Erythrosin

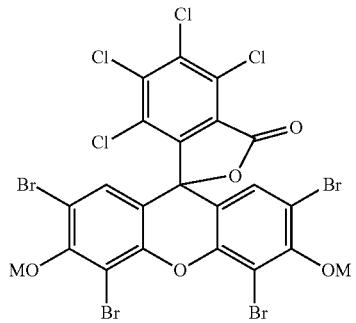

in which M is as defined previously, preferably represents a hydrogen atom or an alkali metal such as sodium;
Magdala Red D&C, Red No. 28
Phloxine B

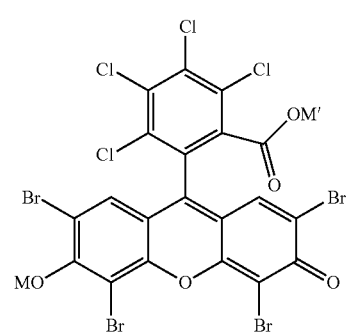

in which M and M' are as defined previously, preferably represent a hydrogen atom or an alkali metal such as sodium;
Magdala Red D&C, Red No. 28
Phloxine B

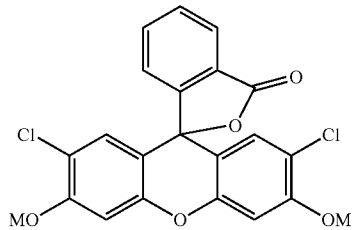

in which M is as defined previously, preferably represents a $(C_1-C_4)$alkylcarbonyl group such as methylcarbonyl;
2,7-dichlorofluorescein -continued

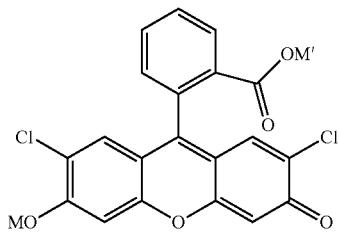

in which M is as defined previously,
preferably represents a (C$_1$-C$_4$)alkylcarbonyl
group such as methylcarbonyl; M' are as defined previously,
preferably represents a hydrogen atom, or an
alkali metal such as sodium;
2,7-dichlorofluorescein

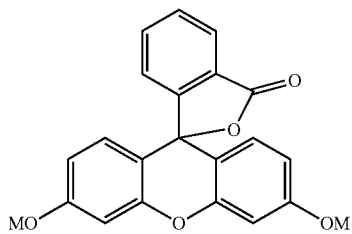

in which M is as defined previously,
preferably represents a hydrogen
atom or an alkali metal such as
sodium or a (C$_1$-C$_4$)alkylcarbonyl
group such as methylcarbonyl;
Fluorescein DC Yellow 7

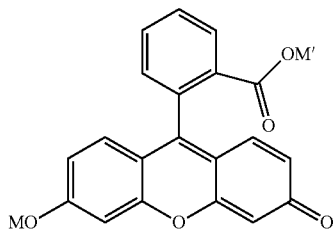

in which M is as defined previously,
preferably represents a hydrogen
atom or an alkali metal such as
sodium or a (C$_1$-C$_4$)alkylcarbonyl
group such as methylcarbonyl;
Fluorescein DC Yellow 7

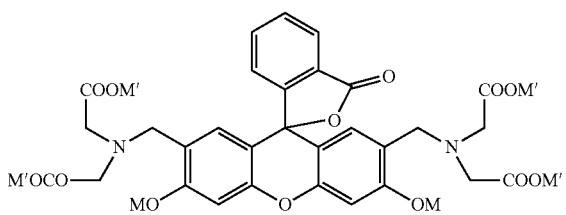

in which M and M' are as defined previously,
preferably represent a hydrogen
atom or an alkali metal such as
sodium;
Eosin

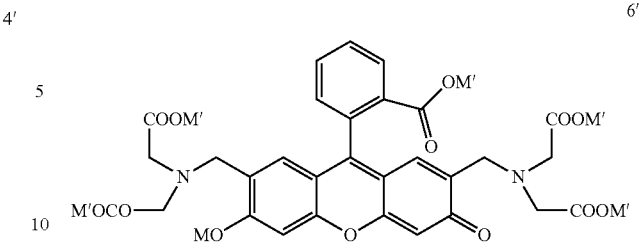

in which M and M' are as defined previously,
preferably represent a hydrogen
atom or an alkali metal such as
sodium;
Eosin According to a preferred embodiment of the invention, composition (A) or (A$_1$) comprises one or more additional dyes, preferably chosen from those of formulae (II) and/or (II') as defined previously in an amount of between 0.001% to 10% by weight, preferably between 0.005% to 5% by weight relative to the total weight of composition (A$_1$).

Compositions (A) or (A$_1$) may also comprise one or more oxidation dyes chosen from the oxidation bases and couplers conventionally used in oxidation dyeing.

Preferably, the oxidation dyes in composition (A) or (A$_1$) particularly represent from 0.001% to 20% and preferably from 0.01% to 10% by weight relative to the total weight of composition (A) or (A$_1$).

ii) The Revealing Step

The process according to the invention involves, after the step of applying composition (A) or (A1) as defined previously, a revealing step using a revelation or revealing composition (B).

The revealing composition (B) is at basic pH, i.e. it is an aqueous composition with a pH of greater than 7, preferably between 7.5 and 12.5, particularly between 8.5 and 12, more particularly between 9 and 11.5.

The revealing composition (B) contains one or more alkaline agents, which may be any agent for increasing the pH of the composition in which it is present. The alkaline agent(s) are chosen from Bronsted-Lowry bases and Lewis bases. They may be mineral or organic.

In particular, the alkaline agent(s) are chosen from:

a) aqueous ammonia, b) alkanolamines, in particular mono-, di- or tri-(C$_1$-C$_6$) alkanolamines such as mono-, di- and triethanolamines, isopropanolamine, 2-amino-2-methyl-1-propanol (AMP), 2-amino-2-methyl-1,3-propanediol (AMPD) and 2-amino-1,3-propanediol, and also derivatives thereof, c) oxyethylenated and/or oxypropylenated (C$_1$-C$_6$)alkylenediamines, d) mineral or organic hydroxides, e) basic amino acids such as arginine, lysine, ornithine, citrulline and histidine, f) alkali metal or alkaline-earth metal silicates or metasilicates such as sodium metasilicates, g) carbonates and bicarbonates, particularly of a primary amine, secondary amine or tertiary amine, or of an alkali metal or alkaline-earth metal, or of ammonium, and h) the compounds of formula (III) below:

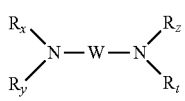

in which formula (III) W represents a divalent $C_1$-$C_6$ alkylene radical optionally substituted with a hydroxyl group or a $C_1$-$C_6$ alkyl radical, $R_x$, $R_y$, $R_z$ and $R_t$, which may be identical or different, represent a hydrogen atom or a $C_1$-$C_6$ alkyl, $C_1$-$C_6$ hydroxyalkyl or $C_1$-$C_6$ aminoalkyl group.

Examples of such compounds of formula (III) that may be mentioned include 1,3-diaminopropane, 1,3-diamino-2-propanol, spermine and spermidine.

The mineral or organic hydroxides are preferably chosen from hydroxides of an alkali metal, hydroxides of an alkaline-earth metal, for instance sodium hydroxide or potassium hydroxide, hydroxides of a transition metal, such as hydroxides of metals from Groups III, IV, V and VI of the Periodic Table of the Elements, hydroxides of lanthanides or actinides, quaternary ammonium hydroxides and guanidinium hydroxide.

The hydroxide may be formed in situ, for instance guanidine hydroxide, by reacting calcium hydroxide and guanidine carbonate.

The preferred alkaline agents are chosen from ammonia, carbonates or bicarbonates such as ammonium or sodium carbonate, ammonium or sodium bicarbonate, basic amino acids such as arginine, alkanolamines such as monoethanolamine (MEA), 2-amino-2-methyl-1-propanol (AMP), 2-amino-2-methyl-1,3-propanediol (AMPD) and 2-amino-1,3-propanediol, preferably alkanolamines such as MEA.

The alkaline agent(s) as defined previously may represent, for example, from 0.1% to 20% by weight, and preferably from 1% to 15% by weight, relative to the total weight of composition (B).

iii) The Switching-Off Step

The process of the invention involves a switching-off step using an acidic composition (C).

Composition (C) is at acidic pH, i.e. it is an aqueous composition with a pH of less than 7, preferably less than 6 and ranging down to 0.5 inclusive, particularly at a pH inclusively between 1 and 5, preferably between 1.3 and 3.

In particular, the switching-off composition (C) comprises one or more organic or mineral acids preferably chosen from i) hydrochloric acid HCl, ii) hydrobromic acid HBr, iii) sulfuric acid $H_2SO_4$, iv) phosphoric or orthophosphoric acid $H_3PO_4$, v) ($C_1$-$C_6$)alkylsulfonic acids: Alk-S(O)$_2$OH, such as methanesulfonic acid and ethanesulfonic acid; vi) arylsulfonic acids: Ar—S(O)$_2$OH such as benzenesulfonic acid and toluenesulfonic acid; vii) carboxylic acids such as acetic acid, tartaric acid, citric acid, lactic acid or succinic acid; viii) sulfonic acids; ix) ($C_1$-$C_6$)alkoxysulfinic acids: Alk-O—S(O)OH such as methoxysulfinic acid and ethoxysulfinic acid; x) aryloxysulfinic acids such as tolueneoxysulfinic acid and phenoxysulfinic acid; xi) triflic acid $CF_3SO_3H$ and xii) tetrafluoroboric acid $HBF_4$. The term "carboxylic acid" means a compound comprising at least one carboxylic acid —C(O)—OH group, preferably of formula (I) as defined previously, preferably comprising between 1 and 4 carboxylic acid groups, such as 1 or 2; chosen from: i) ($C_1$-$C_6$)alkyl-[C(O)—OH]$_n$ and ii) het-[C(O)—OH]$_n$, with n an integer between 1 and 4 inclusive, preferably between 1 and 2, het representing a heterocylic group, such as pyrrolidone, it being possible for the alkyl or het group to be optionally substituted with one or more groups chosen from OH, and (di)($C_1$-$C_4$)(alkyl)amino.

More preferentially, the acids used in the switching-off composition (C) of the invention are chosen from orthophosphoric acid, and carboxylic acids such as acetic acid, tartaric acid, citric acid or lactic acid, more particularly chosen from orthophosphoric acid and carboxylic acid.

The Supports for the Compositions

Compositions (A), ($A_1$), (B) and (C) of the invention are in a cosmetic medium, i.e. a medium that is suitable for dyeing keratin fibers, especially human keratin fibers such as the hair, also known as a dyeing support, which generally comprises water or at least one organic solvent or a mixture of water and of at least one organic solvent.

iv) The Hydrotropic Liquid Organic Compounds

According to one embodiment of the invention, at least one of the compositions (A), ($A_1$), (B) or (C) comprises one or more liquid organic compounds with a Hansen solubility parameter δH of greater than 0 and less than 16 MPa$^{1/2}$. More particularly, composition (A) or ($A_1$) comprising the compound(s) of formula (I) and/or (I') also comprises one or more liquid organic compounds with a Hansen solubility parameter δH of greater than 0 and less than 16 MPa$^{1/2}$. In the context of the present invention, such a liquid organic compound is also known as a hydrotropic compound.

For the purposes of the present invention, the term "hydrotropic compound" means a compound that is capable of increasing the solubility of hydrophobic compounds in aqueous phases.

Said liquid compounds more preferentially have a Hansen solubility parameter δH of between 5 and 15.8 MPa$^{1/2}$, even more preferentially between 8 and 15.8 MPa$^{1/2}$ and better still between 8 and 15 MPa$^{1/2}$.

These compounds are liquid at a temperature of 25° C. and at atmospheric pressure (760 mmHg; i.e. 1.013×10$^5$ Pa).

Compound(s) with a Hansen solubility parameter value δH as defined previously are, for example, described in the reference publication *Hansen solubility parameters: A User's Handbook* by Charles M. Hansen, CRC Press, 2000, pages 167 to 185, or in the publication *Handbook of Solubility Parameters and Other Cohesion Parameters*, CRC Press, pages 95 to 121 and pages 177 to 185.

This value of the solubility parameter δH is related to the formation of hydrogen bonds. It may be recalled that there are three major types of interaction in organic compounds: non-polar interactions, permanent dipole-dipole interactions and interactions of hydrogen bonding type, the latter forming the subject of the parameter defining the hydrotropic compound present in the composition used in accordance with the invention.

In particular, the book *Handbook of Solubility Parameters and Other Cohesion Parameters*, CRC Press, pages 95 to 121 and pages 177 to 185, gives the equation $δH=(Σ-zUh/V)^{1/2}$ in which zUh (in J·mol$^{-1}$) describes the contributions of the functional group considered in the solubility parameters associated with the hydrogen bonds (values in Table 14, page 183), this parameter zUh also being described in the book *The relation between surface tension and solubility parameter in liquids*, Bagda, E, Farbe Lack, 84, 212, 1978; and V is the volume of the molecule.

It should be noted that the value of the solubility parameter δH is usually given for a temperature of 25° C. and at atmospheric pressure (760 mmHg, i.e. 1.013×10$^5$ Pa).

In particular, the liquid organic compounds with a Hansen solubility parameter value δH of greater than 0 and less than 16 MPa$^{1/2}$ are nonionic compounds.

Preferably, said liquid organic compound(s) with a Hansen solubility parameter value δH of greater than 0 and less than 16 MPa$^{1/2}$ are chosen from alcohol ethers, aliphatic esters, aliphatic ethers, aromatic ethers, alkanols bearing aryl substituents, lactones and sulfones, and mixtures thereof.

Said liquid organic compound(s) with a Hansen solubility parameter value δH of greater than 0 and less than 16 MPa$^{1/2}$ may be chosen from:
- alcohol ethers, in particular $C_1$-$C_4$ ethers of $C_5$-$C_{30}$ alcohols, which are preferably saturated, linear or branched, optionally interrupted with one or more non-adjacent ether functions;
- aliphatic esters of $C_1$-$C_4$ carboxylic acids and of $C_3$-$C_{10}$ monoalcohols or polyhydroxylated alcohols, interrupted with one or more non-adjacent ether functions;
- aromatic ethers, in particular of $C_6$-$C_{10}$, of a $C_1$-$C_6$ alkyl optionally bearing a hydroxyl group;
- ($C_6$-$C_{10}$)aryl($C_1$-$C_6$)alkyl ethers of a $C_1$-$C_6$ alkyl optionally bearing a hydroxyl group;
- alkanols bearing an aryl substituent, preferably for which the aryl part is $C_6$-$C_{10}$, advantageously $C_6$, and the alkyl part of the alkanol is $C_1$-$C_4$, this alkyl part possibly ending or being interrupted with a heteroatom, advantageously oxygen or a hydroxyl group, preferably such as benzyl alcohol;
- lactones preferably of formula (iii), and also mixtures thereof, with:

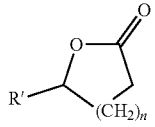

in which formula (iii) R' represents a hydrogen, a linear or branched $C_1$-$C_8$ alkyl or a linear or branched $C_1$-$C_4$ hydroxyalkyl and n has the value 1, 2 or 3, and preferably R' represents a hydrogen, a linear or branched $C_1$-$C_6$ alkyl or a linear or branched $C_1$-$C_2$ hydroxyalkyl;
- sulfones, especially cyclic sulfones, in particular sulfolanes, preferably substituted with one or more ($C_1$-$C_4$) alkyl groups such as 3-methyl sulfolane.

Mention may be made, as particularly advantageous examples of lactones, of γ-butyrolactone.

Mention may also be made of certain liquid alkanols, for instance 1-pentanol.

Even more preferentially, said liquid organic compound(s) according to the invention are chosen from dipropylene glycol monomethyl ether acetate, dipropylene glycol methyl ether, dipropylene glycol mono-n-butyl ether (the INCI name of which is PPG-2 Butyl Ether), tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol and phenoxyethanol, and mixtures of these compounds.

In particular, the liquid organic compound with a Hansen solubility parameter δH of greater than 0 and less than 16 MPa$^{1/2}$ is preferably chosen from i) alcohol ethers, ii) aliphatic esters, iii) aromatic ethers, iv) alkanols bearing aryl substituents, preferably for which the aryl part is $C_6$-$C_{10}$, advantageously $C_6$, and the alkyl part of the alkanol is $C_1$-$C_4$, this alkyl part possibly being terminated or interrupted with a heteroatom, advantageously oxygen, or a hydroxyl group, preferably such as benzyl alcohol and phenoxyethanol, v) 5- to 7-membered cyclic sulfones optionally substituted with one or more ($C_1$-$C_4$)alkyl groups such as 3-methyl sulfolane, and mixtures thereof.

According to a particular embodiment of the invention, the liquid organic compound(s) with a Hansen solubility parameter value δH of greater than 0 and less than 16 MPa$^{1/2}$ are chosen from aromatic alcohols, and mixtures thereof; even more preferentially chosen from alkanols bearing aryl substituents and even more preferentially benzyl alcohol and/or phenoxyethanol. In particular, benzyl alcohol is present in an amount of between 1% and 10%, such as 5% by weight relative to the total weight of composition (A), ($A_1$), (B) or (C), more particularly composition (A) or ($A_1$); and phenoxyethanol is present in an amount of between 0.5% and 3%, such as 1% by weight relative to the total weight of composition (A), ($A_1$), (B) or (C), more particularly composition (A) or ($A_1$).

When it is (they are) present, the liquid organic compound(s) with a Hansen solubility parameter value δH of greater than 0 and less than 16 MPa$^{1/2}$ preferably represent a total content ranging from 0.05% to 35% by weight, preferably from 1% to 20% by weight, better still from 2% to 10% by weight, in particular between 5% and 7%, such as 6% by weight relative to the total weight of composition (A), ($A_1$), (B) or (C), more particularly composition (A) or ($A_1$).

v) The Non-Hydrotropic Organic Solvents

According to one embodiment of the invention, at least one of the compositions of the process of the invention comprises one or more additional organic solvents (other than the liquid organic compound(s) with a Hansen solubility parameter δH of greater than 0 and less than or equal to 16 MPa$^{1/2}$). More particularly, composition (A) or ($A_1$) comprising the compound(s) of formula (I) or (I') comprises one or more additional organic solvents (other than the liquid organic compound(s) with a Hansen solubility parameter δH of greater than 0 and less than or equal to 16 MPa$^{1/2}$). Additional organic solvents that may particularly be mentioned include $C_1$-$C_4$ lower alkanols, such as ethanol and isopropanol; polyols and polyol ethers. Additional organic solvents that may more particularly be mentioned include $C_2$-$C_4$ lower alkanols, such as ethanol and isopropanol; polyols and polyol ethers.

At least one of the compositions of the process according to the invention preferably comprises one or more $C_1$-$C_4$ lower alkanols, such as ethanol or isopropanol, more preferably one or more $C_2$-$C_4$ lower alkanols, such as ethanol or isopropanol.

Particularly, composition (A) or ($A_1$) comprising the compound(s) of formula (I) or (I') preferably comprises one or more $C_1$-$C_4$ lower alkanols, such as ethanol or isopropanol, more preferably one or more $C_2$-$C_4$ lower alkanols, such as ethanol or isopropanol Preferably, at least one of the compositions of the process according to the invention, more preferentially composition (A) or ($A_1$) comprising the compound(s) of formula (I) or (I') comprises ethanol.

The additional organic solvents (other than the liquid organic compound(s) with a Hansen solubility parameter value δH of greater than 0 and less than 16 MPa$^{1/2}$) may be present in a total content preferably between 1% and 40% by weight and even more preferentially between 5% and 30% by weight approximately relative to the total weight of the composition which contains them, in particular relative to the total weight of composition (A) or ($A_1$).

vi) The Thickeners

According to one embodiment of the invention, at least one of the compositions (A), ($A_1$), (B) or (C) also comprises one or more thickeners, preferably polymeric thickeners. More particularly, composition (A) or ($A_1$) also comprises one or more thickeners preferably chosen from associative or non-associative cationic, nonionic, anionic or zwitterionic organic polymers, of natural or synthetic origin.

Thickening polymers that may be mentioned include non-associative thickening polymers bearing sugar units.

For the purposes of the present invention, the term "sugar unit" means a unit derived from a carbohydrate of formula $C_n(H_2O)_{n-1}$ or $(CH_2O)_n$, which may be optionally modified by substitution and/or by oxidation and/or by dehydration.

The sugar units of the thickening polymers of the invention are preferably derived from the following sugars:
glucose;
galactose;
arabinose;
rhamnose;
mannose;
xylose;
fucose;
anhydrogalactose;
galacturonic acid;
glucuronic acid;
mannuronic acid;
galactose sulfate;
anhydrogalactose sulfate and
fructose.

Thickening polymers of the invention that may in particular be mentioned include native gums such as:

a) tree or shrub exudates, including:
gum arabic (branched polymer of galactose, arabinose, rhamnose and glucuronic acid);
ghatti gum (polymer derived from arabinose, galactose, mannose, xylose and glucuronic acid);
karaya gum (polymer derived from galacturonic acid, galactose, rhamnose and glucuronic acid);
gum tragacanth (or tragacanth) (polymer of galacturonic acid, galactose, fucose, xylose and arabinose);

b) gums derived from algae, including:
agar (polymer derived from galactose and anhydrogalactose);
alginates (polymers of mannuronic acid and of glucuronic acid);
carrageenans and furcellerans (polymers of galactose sulfate and of anhydrogalactose sulfate);

c) gums derived from seeds or tubers, including:
guar gum (polymer of mannose and galactose);
locust bean gum (polymer of mannose and galactose);
fenugreek gum (polymer of mannose and galactose);
tamarind gum (polymer of galactose, xylose and glucose);
konjac gum (polymer of glucose and mannose);

d) microbial gums, including:
xanthan gum (polymer of glucose, mannose acetate, mannose/pyruvic acid and glucuronic acid);
gellan gum (polymer of partially acylated glucose, rhamnose and glucuronic acid);
scleroglucan gum (glucose polymer);

e) plant extracts, including:
cellulose (glucose polymer);
starch (glucose polymer) and
inulin.

These polymers can be physically or chemically modified. As physical treatment, mention may in particular be made of the temperature.

Chemical treatments that may be mentioned include esterification, etherification, amidation and oxidation reactions. These treatments make it possible to lead to polymers that may in particular be nonionic, anionic or amphoteric.

Preferably, these chemical or physical treatments are applied to guar gums, locust bean gums, starches and celluloses.

The nonionic guar gums that may be used according to the invention may be modified with $C_1$-$C_6$ (poly)hydroxyalkyl groups.

Among the $C_1$-$C_6$ (poly)hydroxyalkyl groups, mention may be made, by way of example, of hydroxymethyl, hydroxyethyl, hydroxypropyl and hydroxybutyl groups.

These guar gums are well known from the prior art and may be prepared, for example, by reacting corresponding alkene oxides, for instance propylene oxides, with the guar gum so as to obtain a guar gum modified with hydroxypropyl groups.

The degree of hydroxyalkylation preferably varies from 0.4 to 1.2 and corresponds to the number of alkylene oxide molecules consumed by the number of free hydroxyl functional groups present on the guar gum.

Such nonionic guar gums optionally modified with hydroxyalkyl groups are sold, for example, under the trade names Jaguar HP8, Jaguar HP60 and Jaguar HP120 by the company Rhodia Chimie.

The botanical origin of the starch molecules used in the present invention may be cereals or else tubers. Thus, the starches are chosen, for example, from corn starch, rice starch, cassava starch, barley starch, potato starch, wheat starch, sorghum starch and pea starch.

The starches may be chemically or physically modified, in particular by one or more of the following reactions: pregelatinization, oxidation, crosslinking, esterification, etherification, amidation, heat treatments.

Distarch phosphates or compounds rich in distarch phosphate will preferentially be used, for instance the product sold under the references Prejel VA-70-T AGGL (gelatinized hydroxypropyl cassava distarch phosphate), Prejel TK1 (gelatinized cassava distarch phosphate) and Prejel 200 (gelatinized acetyl cassava distarch phosphate) by the company Avebe, or Structure Zea from National Starch (gelatinized corn distarch phosphate).

According to the invention, amphoteric starches may also be used, these amphoteric starches comprising one or more anionic groups and one or more cationic groups. The anionic and cationic groups may be bonded to the same reactive site of the starch molecule or to different reactive sites; they are preferably bonded to the same reactive site. The anionic groups may be of carboxylic, phosphate or sulfate type, preferably carboxylic. The cationic groups may be of primary, secondary, tertiary or quaternary amine type.

The starch molecules may be derived from any plant source of starch, in particular such as corn, potato, oat, rice, tapioca, sorghum, barley or wheat. It is also possible to use the hydrolyzates of the starches mentioned above. The starch is preferably derived from potato.

The non-associative thickening polymers of the invention may be cellulose-based polymers not including a $C_{10}$-$C_{30}$ fatty chain in their structure.

According to the invention, the term "cellulose-based" polymer means any polysaccharide compound having in its structure sequences of glucose residues linked together via β-1,4 bonds; in addition to unsubstituted celluloses, the cellulose derivatives may be anionic, cationic, amphoteric or nonionic.

Thus, the cellulose-based polymers of the invention may be chosen from unsubstituted celluloses, including those in a microcrystalline form, and cellulose ethers.

Among these cellulose-based polymers, cellulose ethers, cellulose esters and cellulose ester ethers are distinguished.

Among the cellulose esters are mineral esters of cellulose (cellulose nitrates, sulfates, phosphates, etc.), organic cellulose esters (cellulose monoacetates, triacetates, amidopropionates, acetatebutyrates, acetatepropionates and acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Among the nonionic cellulose ethers without a $C_{10}$-$C_{30}$ fatty chain, i.e. which are "non-associative", mention may be made of ($C_1$-$C_4$)alkylcelluloses, such as methylcelluloses and ethylcelluloses (for example, Ethocel standard 100 Premium from Dow Chemical); (poly)hydroxy($C_1$-$C_4$)alkylcelluloses, such as hydroxymethylcelluloses, hydroxyethylcelluloses (for example, Natrosol 250 HHR provided by Aqualon) and hydroxypropylcelluloses (for example, Klucel EF from Aqualon); mixed (poly)hydroxy($C_1$-$C_4$)alkyl-($C_1$-$C_4$)alkylcelluloses, such as hydroxypropylmethylcelluloses (for example, Methocel E4M from Dow Chemical), hydroxyethylmethylcelluloses, hydroxyethylethylcelluloses (for example, Bermocoll E 481 FQ from Akzo Nobel) and hydroxybutylmethylcelluloses.

Among the anionic cellulose ethers without a fatty chain, mention may be made of (poly)carboxy($C_1$-$C_4$)alkylcelluloses and salts thereof. By way of example, mention may be made of carboxymethylcelluloses, carboxymethylmethylcelluloses (for example Blanose 7M from the company Aqualon) and carboxymethylhydroxyethylcelluloses, and the sodium salts thereof.

Among the cationic cellulose ethers without a fatty chain, mention may be made of cationic cellulose derivatives such as cellulose copolymers or cellulose derivatives grafted with a water-soluble quaternary ammonium monomer, and described in particular in U.S. Pat. No. 4,131,576, such as (poly)hydroxy($C_1$-$C_4$)alkyl celluloses, for instance hydroxymethyl-, hydroxyethyl- or hydroxypropylcelluloses grafted in particular with a methacryloylethyltrimethylammonium, methacrylamidopropyltrimethylammonium or dimethyldiallylammonium salt. The commercial products corresponding to this definition are more particularly the products sold under the names Celquat® L 200 and Celquat® H 100 by the company National Starch.

Among the non-associative thickening polymers not bearing sugar units that may be used, mention may be made of crosslinked acrylic acid or methacrylic acid homopolymers or copolymers, crosslinked 2-acrylamido-2-methylpropanesulfonic acid homopolymers and crosslinked acrylamide copolymers thereof, ammonium acrylate homopolymers, or copolymers of ammonium acrylate and of acrylamide, alone or as mixtures thereof.

A first family of non-associative thickening polymers that is suitable for use is represented by crosslinked acrylic acid homopolymers.

Among the homopolymers of this type, mention may be made of those crosslinked with an allyl alcohol ether of the sugar series, for instance, the products sold under the names Carbopol 980, 981, 954, 2984 and 5984 by the company Noveon or the products sold under the names Synthalen M and Synthalen K by the company 3 VSA.

The non-associative thickening polymers may also be crosslinked (meth)acrylic acid copolymers, such as the polymer sold under the name Aqua SF1 by the company Noveon.

The non-associative thickening polymers may be chosen from crosslinked 2-acrylamido-2-methylpropanesulfonic acid homopolymers and the crosslinked acrylamide copolymers thereof.

Among the partially or totally neutralized crosslinked copolymers of 2-acrylamido-2-methylpropanesulfonic acid and of acrylamide, mention may be made in particular of the product described in Example 1 of document EP 503 853, and reference may be made to said document as regards these polymers.

The composition may similarly comprise, as non-associative thickening polymers, ammonium acrylate homopolymers or copolymers of ammonium acrylate and of acrylamide.

Among the examples of ammonium acrylate homopolymers that may be mentioned is the product sold under the name Microsap PAS 5193 by the company Hoechst. Among the copolymers of ammonium acrylate and of acrylamide that may be mentioned is the product sold under the name Bozepol C Nouveau or the product PAS 5193 sold by the company Hoechst. Reference may be made especially to FR 2 416 723, U.S. Pat. Nos. 2,798,053 and 2,923,692 as regards the description and preparation of such compounds.

Among the aqueous-phase thickening polymers, mention may also be made of the non-cellulose-based associative polymers that are well known to those skilled in the art and in particular of nonionic, anionic, cationic or amphoteric nature.

It is recalled that "associative polymers" are polymers that are capable, in an aqueous medium, of reversibly associating with each other or with other molecules.

Their chemical structure more particularly comprises at least one hydrophilic region and at least one hydrophobic region.

The term "hydrophobic group" means a radical or polymer with a saturated or unsaturated, linear or branched hydrocarbon-based chain, comprising at least 10 carbon atoms, preferably from 10 to 30 carbon atoms, in particular from 12 to 30 carbon atoms and more preferentially from 18 to 30 carbon atoms.

Preferentially, the hydrocarbon-based group is derived from a monofunctional compound. By way of example, the hydrophobic group may be derived from a fatty alcohol such as stearyl alcohol, dodecyl alcohol or decyl alcohol. It may also denote a hydrocarbon-based polymer, for instance polybutadiene.

Among the associative polymers of anionic type that may be mentioned are:
(a) those including at least one hydrophilic unit and at least one fatty-chain allyl ether unit, more particularly those of which the hydrophilic unit is constituted by an ethylenic unsaturated anionic monomer, more particularly still a vinylcarboxylic acid and most particularly an acrylic acid or a methacrylic acid or mixtures thereof.

Among these anionic associative polymers, those that are particularly preferred according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether, and from 0 to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl alcohol ether (Steareth-10), in particular those sold by the company Ciba under the names Salcare SC 80® and Salcare SC 90®, which are aqueous 30% emulsions of a crosslinked terpolymer of methacrylic acid, of ethyl acrylate and of steareth-10 allyl ether (40/50/10);

(b) those including i) at least one hydrophilic unit of unsaturated olefinic carboxylic acid type, and ii) at least one hydrophobic unit of the ($C_{10}$-$C_{30}$) alkyl ester of an unsaturated carboxylic acid type.

($C_{10}$-$C_{30}$) Alkyl esters of unsaturated carboxylic acids that are useful in the invention comprise, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among anionic associative polymers of this type, use will more particularly be made of those constituted of 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or else of those constituted of 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1®, Pemulen TR2® and Carbopol 1382®, and even more preferentially Pemulen TR1®, and the product sold by the company SEPPIC under the name Coatex SX®.

Mention may also be made of the acrylic acid/lauryl methacrylate/vinylpyrrolidone terpolymer sold under the name Acrylidone LM by the company ISP.

(c) maleic anhydride/$C_{30}$-$C_{38}$ α-olefin/alkyl maleate terpolymers, such as the product (maleic anhydride/$C_{30}$-$C_{38}$ α-olefin/isopropyl maleate copolymers) sold under the name Performa V 1608® by the company Newphase Technologies.

(d) acrylic terpolymers comprising:
i) about 20% to 70% by weight of an α,β-monoethylenically unsaturated carboxylic acid [A],
ii) about 20% to 80% by weight of an α,β-monoethylenically unsaturated non-surfactant monomer other than [A],
iii) about 0.5% to 60% by weight of a nonionic monourethane which is the product of reaction of a monohydric surfactant with a monoethylenically unsaturated monoisocyanate, such as those described in patent application EP-A-0 173 109 and more particularly the terpolymer described in Example 3, namely a methacrylic acid/methyl acrylate/behenyl alcohol dimethyl-meta-isopropenylbenzylisocyanate ethoxylated (40 EO) terpolymer, as an aqueous 25% dispersion.

(e) copolymers including among their monomers an α,β-monoethylenically unsaturated carboxylic acid and an ester of an α,β-monoethylenically unsaturated carboxylic acid and of an oxyalkylenated fatty alcohol.

Preferably, these compounds also comprise as monomer an ester of an α,β-monoethylenically unsaturated carboxylic acid and of a $C_1$-$C_4$ alcohol.

An example of a compound of this type that may be mentioned is Aculyn 22® sold by the company Röhm & Haas, which is a methacrylic acid/ethyl acrylate/oxyalkylenated stearyl methacrylate terpolymer;

(f) amphiphilic polymers including at least one ethylenically unsaturated monomer bearing a sulfonic group, in free or partially or totally neutralized form and comprising at least one hydrophobic part. These polymers may be crosslinked or non-crosslinked. They are preferably crosslinked.

The ethylenically unsaturated monomers bearing a sulfonic group are in particular chosen from vinylsulfonic acid, styrenesulfonic acid, (meth)acrylamido($C_1$-$C_{22}$)alkylsulfonic acids, N—($C_1$-$C_{22}$)alkyl(meth)acrylamido($C_1$-$C_{22}$)alkylsulfonic acids such as undecylacrylamidomethanesulfonic acid, and also partially or totally neutralized forms thereof.

(Meth)acrylamido($C_1$-$C_{22}$)alkylsulfonic acids, for instance acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferentially be used.

2-Acrylamido-2-methylpropanesulfonic acid (AMPS), and also partially or totally neutralized forms thereof, will more particularly be used.

The polymers of this family may be chosen especially from random amphiphilic AMPS polymers modified by reaction with a $C_6$-$C_{22}$ n-monoalkylamine or di-n-alkylamine, and such as those described in patent application WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid and maleic acid, or mixtures of these compounds.

The preferred polymers of this family are chosen from amphiphilic copolymers of AMPS and of at least one ethylenically unsaturated hydrophobic monomer.

These same copolymers may also contain one or more ethylenically unsaturated monomers not including a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid and maleic acid, or mixtures of these compounds.

These copolymers are described especially in patent application EP-A-0 750 899, U.S. Pat. No. 5,089,578 and in the following publications from Yotaro Morishima:

Self-assembling amphiphilic polyelectrolytes and their nanostructures, Chinese Journal of Polymer Science, Vol. 18, No. 40, (2000), 323-336;

Micelle formation of random copolymers of sodium 2-(acrylamido)-2-methylpropanesulfonate and a nonionic surfactant macromonomer in water as studied by fluorescence and dynamic light scattering—*Macromolecules*, Vol. 33, No. 10 (2000), 3694-3704;

Solution properties of micelle networks formed by nonionic moieties covalently bound to a polyelectrolyte: salt effects on rheological behavior—*Langmuir*, ol. 16, No. 12, (2000) 5324-5332;

Stimuli responsive amphiphilic copolymers of sodium 2-(acrylamido)-2-methylpropanesulfonate and associative macromonomers—*Polym. Preprint, Div. Polym. Chem.*, 40(2), (1999), 220-221.

Among these polymers, mention may be made of:
crosslinked or non-crosslinked, neutralized or non-neutralized copolymers, including from 15% to 60% by weight of AMPS units and from 40% to 85% by weight of ($C_8$-$C_{16}$)alkyl(meth)acrylamide or ($C_8$-$C_{16}$)alkyl (meth)acrylate units relative to the polymer, such as those described in patent application EP-A750 899;

terpolymers including from 10 mol % to 90 mol % of acrylamide units, from 0.1 mol % to 10 mol % of AMPS units and from 5 mol % to 80 mol % of n-($C_6$-$C_{18}$)alkylacrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Among the cationic associative polymers, mention may be made of:
(I) cationic associative polyurethanes;
(II) the compound sold by the company Noveon under the name Aqua CC and which corresponds to the INCI name Polyacrylate-1 Crosspolymer.

Polyacrylate-1 Crosspolymer is the product of polymerization of a monomer mixture comprising:
a di($C_1$-$C_4$ alkyl)amino($C_1$-$C_6$ alkyl) methacrylate,
one or more $C_1$-$C_{30}$ alkyl esters of (meth)acrylic acid,
a polyethoxylated $C_{10}$-$C_{30}$ alkyl methacrylate (20-25 mol of ethylene oxide units),
a 30/5 polyethylene glycol/polypropylene glycol allyl ether,
a hydroxy($C_2$-$C_6$ alkyl) methacrylate, and
an ethylene glycol dimethacrylate.

(III) quaternized (poly)hydroxyethylcelluloses modified with groups including at least one fatty chain, such as alkyl, arylalkyl or alkylaryl groups including at least 8 carbon atoms, or mixtures thereof. The alkyl radicals borne by the above quaternized celluloses or hydroxyethylcelluloses preferably include from 8 to 30 carbon atoms. The aryl radicals preferably denote phenyl, benzyl, naphthyl or anthryl groups. Examples of quaternized alkylhydroxyethylcelluloses containing $C_8$-$C_{30}$ fatty chains that may be indicated include the products Quatrisoft LM 200®, Quatrisoft LM-X 529-18-A®, Quatrisoft LM-X 529-18-B® ($C_{12}$ alkyl) and Quatrisoft LM-X 529-8® ($C_{18}$ alkyl) sold by the company Aqualon, and the products Crodacel QM®, Crodacel QL® ($C_{12}$ alkyl) and Crodacel QS® ($C_{18}$ alkyl) sold by the company Croda and the product Softcat SL 100® sold by the company Aqualon.

(IV) cationic polyvinyllactam polymers.
Such polymers are described, for example, in patent application WO-00/68282.

As cationic poly(vinyllactam) polymers according to the invention, vinylpyrrolidone/dimethylaminopropylmethacrylamide/dodecyldimethylmethacryl-amidopropylammonium tosylate terpolymers, vinylpyrrolidone/dimethylaminopropylmethacrylamide/cocoyldimethylmethacryl-amidopropylammonium tosylate terpolymers, vinylpyrrolidone/dimethylaminopropylmethacrylamide/lauryldimethylmethacrylamidopropylammonium tosylate or chloride terpolymers are used in particular.

The amphoteric associative polymers are preferably chosen from those including at least one noncyclic cationic unit. Even more particularly, those prepared from or comprising 1 to 20 mol %, preferably 1.5 to 15 mol % and even more particularly 1.5 to 6 mol % of fatty-chain monomer relative to the total number of moles of monomers are preferred.

Amphoteric associative polymers according to the invention are described and prepared, for example, in patent application WO 98/44012.

Among the amphoteric associative polymers according to the invention, the ones that are preferred are acrylic acid/(meth)acrylamidopropyltrimethylammonium chloride/stearyl methacrylate terpolymers.

The associative polymers of nonionic type that may be used according to the invention are preferably chosen from:
(a) copolymers of vinylpyrrolidone and of fatty-chain hydrophobic monomers, of which examples that may be mentioned include:
the products Antaron V216® or Ganex V216® (vinylpyrrolidone/hexadecene copolymer) sold by the company I.S.P.
the products Antaron V220® or Ganex V220® (vinyl pyrrolidone/eicosene copolymer) sold by the company I.S.P.;
(b) copolymers of $C_1$-$C_6$ alkyl methacrylates or acrylates and of amphiphilic monomers comprising at least one fatty chain, for instance, the oxyethylenated methyl acrylate/stearyl acrylate copolymer sold by the company Goldschmidt under the name Antil 208®.
(c) copolymers of hydrophilic methacrylates or acrylates and of hydrophobic monomers including at least one fatty chain, for instance the polyethylene glycol methacrylate/lauryl methacrylate copolymer;
(d) polyurethane polyethers including in their chain both hydrophilic blocks usually of polyoxyethylenated nature and hydrophobic blocks, which may be aliphatic sequences alone and/or cycloaliphatic and/or aromatic sequences;
(e) polymers with an aminoplast ether backbone containing at least one fatty chain, such as the Pure Thix® compounds sold by the company Sud-Chemie.
(f) celluloses or derivatives thereof, modified with groups including at least one fatty chain, such as alkyl, arylalkyl or alkylaryl groups or mixtures thereof wherein the alkyl groups are of $C_8$, and in particular:
nonionic alkylhydroxyethylcelluloses such as the products Natrosol Plus Grade 330 CS and Polysurf 67 ($C_{16}$ alkyl) sold by the company Aqualon;
nonionic nonoxynylhydroxyethylcelluloses such as the product Amercell HM-1500 sold by the company Amerchol;
nonionic alkylcelluloses such as the product Bermocoll EHM 100 sold by the company Berol Nobel;
(g) associative guar derivatives, for instance hydroxypropyl guars modified with a fatty chain, such as the product Esaflor HM 22 (modified with a $C_{22}$ alkyl chain) sold by the company Lamberti; the product Miracare XC 95-3 (modified with a $C_{14}$ alkyl chain) and the product RE 205-146 (modified with a $C_{20}$ alkyl chain) sold by Rhodia Chimie.

Preferably, the polyurethane polyethers include at least two hydrocarbon-based lipophilic chains containing from 6 to 30 carbon atoms, separated by a hydrophilic block, the hydrocarbon-based chains possibly being side chains or chains at the end of the hydrophilic block. In particular, it is possible for one or more pendent chains to be envisaged. In addition, the polymer may include a hydrocarbon-based chain at one end or at both ends of a hydrophilic block.

The polyurethane polyethers may be multiblock, in particular in triblock form. The hydrophobic blocks may be at each end of the chain (for example: triblock copolymer bearing a hydrophilic central block) or distributed both at the ends and in the chain (for example, multiblock copolymer). These same polymers may also be graft polymers or star polymers.

The nonionic fatty-chain polyurethane polyethers may be triblock copolymers, the hydrophilic block of which is a polyoxyethylene chain including from 50 to 1000 oxyethylene groups. The nonionic polyurethane polyethers include a urethane bond between the hydrophilic blocks, hence the origin of the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a $C_{18}$ alkyl chain, from Akzo.

The product DW 1206B® from Röhm & Haas containing a $C_{20}$ alkyl chain and a urethane bond, sold at a solids content of 20% in water, may also be used.

Use may also be made of solutions or dispersions of these polymers, especially in water or in aqueous-alcoholic medium. Examples of such polymers that may be mentioned are Rheolate® 255, Rheolate® 278 and Rheolate® 244 sold by the company Rheox. Use may also be made of the products DW 1206F and DW 1206J sold by the company Röhm & Haas.

The polyurethane polyethers that may be used according to the invention are in particular those described in the article by G. Fonnum, J. Bakke and Fk. Hansen—*Colloid Polym. Sci.*, 271, 380-389 (1993).

It is even more particularly preferred to use a polyurethane polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold in particular by the company Röhm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

Preferably, the polymers in the cosmetic compositions in accordance with the present invention advantageously have in solution or in dispersion, at 1% active material in water, a viscosity, measured using a Rheomat RM 180 rheometer at 25° C., of greater than 0.1 ps and even more advantageously greater than 0.2 cp, at a shear rate of 200 $s^{-1}$.

Preferably, the thickener(s) are chosen from polysaccharides, in particular cellulose polymers, and more particularly hydroxy($C_{1-4}$)alkylcelluloses such as hydroxyethylcelluloses (HEC), hydroxypropylmethylcelluloses (HPMC), xanthan gums, guar gums and polyvinylpyrrolidones (PVP).

According to a particular mode of the invention, the organic thickening polymer(s) are chosen from cellulose polymers, and more particularly hydroxy($C_1$-$C_4$)alkylcelluloses such as hydroxyethylcelluloses (HEC) and hydroxypropylmethylcelluloses (HPMC).

When they are present, the organic thickening polymer(s) represent a total content ranging from 0.01% to 10% by weight and preferably from 0.1% to 5% by weight relative to the total weight of composition (A), ($A_1$), (B) or (C) and preferably (A) or ($A_1$).

Compositions (A), ($A_1$), (B) or (C) of the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof other than the thickening polymers described previously, antioxidants, penetrants, sequestrants, fragrances, dispersants, cations, film-forming agents, ceramides, preserving agents and opacifiers.

When they are present, the above adjuvants generally represent an amount for each of them of between 0.01% and 20% by weight relative to the weight of composition (A), ($A_1$), (B) or (C).

The pH of composition (A), ($A_1$), (B) or (C) may be adjusted to the desired value by means of alkaline agents as defined previously in ii) or by using acids as defined previously in iii), or alternatively by means of standard buffer systems.

The compositions according to the invention may be in various forms, such as in the form of liquids, creams or gels, or in any other form that is suitable for dyeing keratin fibers, and especially human hair.

The process of the invention makes it possible especially to obtain colors that change or colouration of which the color disappears and then reappears (switch off-switch on), or appears and disappears (switch on-switch off) within a pH zone that does not impair the keratin fibers and without any substantial loss of color, especially in terms of color intensity or color build-up.

The process of the invention makes it possible especially to obtain changing colors or whose color disappears and then reappears (switch off-switch on), or appears and disappears (switch on-switch off) within a pH zone that does not impair the keratin fibers and without any substantial loss of color, especially in terms of color intensity or color build-up.

Furthermore, the process of the invention makes it possible to obtain keratin fiber colorings with intense colors, and a good color build-up which can switch as a function of the pH, even after several cycles, with a rapid and sharp effect of the "switch off-switch on" color change, with structured effects (geometrical, graphic, etc. effect), without any color transfer from one lock to another (e.g. possibility on a braid comprising three dyes of different colors of there being no color diffusion from one lock to another even after several pH revealing cycles), and which can avoid denaturing of the keratin fibers.

For the purposes of the present invention, the coloring is erased or switched off when the keratin fibers have regained their original color. The coloring is modified when the coloring obtained is different from that obtained during the preceding step. The coloring is reformed when the coloring obtained on the keratin fibers is identical to that which was obtained during a preceding step and which was subsequently modified. The coloring obtained depends on the compound(s) of formula (I) or (I') that are applied to the keratin fibers. When all of these compounds have their sulfonate ring open like the compounds (I'), the coloring is intense and chromatic. By modifying the pH, it is possible to erase this coloring by going from all of the compounds of formula (I'), the sulfonate ring of which is open, to all of the compounds of formula (I), the sulfonate ring of which is closed, and then to reform it by going from all of the compounds of formula (I), the sulfonate ring of which is closed, to all of the compounds of formula (I'), the sulfonate ring of which is open. It is also possible to vary the ratio between the concentration of compounds of formula (I'), the sulfonate ring of which is open, and the concentration of compounds of formula (I), the sulfonate ring of which is closed. The coloring is then modified in intensity and/or chromaticity depending on whether the keratin fibers are treated with one or more compounds of formula (I), the sulfonate ring of which is closed, or one or more compounds of formula (I'), the sulfonate ring of which is open, and depending on their relative pH sensitivity.

According to a particular embodiment, the process of the invention is performed on light-colored keratin fibers in particular with a tone depth (European scale) of between 8 and 10.

The "tone depth" is the unit known to hairstyling professionals, and published in the book "Science des traitements capillaires [Science of hair treatment]" by Charles Zviak 1988, published by Masson, pages 215 and 278; the tone depths range, according to the European scale, from 1 (black) to 10 (very light blond), one unit corresponding to one tone, the higher the figure, the lighter the shade;

According to another particular embodiment, the process is performed on dark keratin fibers, in particular chestnut-brown fibers with a tone depth (European scale) of less than or equal to 6, preferably less than or equal to 4.

A "dark" keratin fiber is a keratin fiber whose lightness $L^*$ measured in the CIE $L^*a^*b^*$ system is less than or equal to 45 and preferably less than or equal to 40, given that $L^*=0$ is equivalent to black and $L^*=100$ is equivalent to white.

On dark keratin fibers treated with the compounds of formula (I) or (I') and after application of the revealing composition (B), the color appears up to black, with blue-green or more natural coppery chromatic tints which disappear after application of the switching-off composition (C).

According to a particular embodiment of the invention for treating keratin fibers, and in particular human keratin fibers such as the hair, the process is characterized in that the following steps are performed:
i) a step of applying a composition (A) or ($A_1$), comprising one or more triarylmethane or sulfonophthalein compounds of formula (I) as defined previously, preferably at the acidic pH for which the compound is weakly colored or even colorless;
then
ii) a revealing step which consists in applying to said fibers a composition (B) at basic pH;
then
iii) a switching-off step which consists in applying to said fibers a composition (C) at acidic pH;
it being understood that steps ii) and iii) may be repeated several times.

According to a particular embodiment of the invention for treating keratin fibers, and in particular human keratin fibers such as the hair, the process is characterized in that the following steps are performed:
i) a step of applying a composition (A) or ($A_1$) comprising one or more compounds chosen from: (1), (2), (3), (4) and (5),
then
ii) a revelation step which consists in applying to said fibers a composition (B) at basic pH;
then
iii) a switching-off step which consists in applying to said fibers a composition (C) at acidic pH;
it being understood that steps ii) and iii) may be repeated several times.

According to another particular embodiment of the invention for treating keratin fibers, and in particular human keratin fibers such as the hair, the process is characterized in that the following steps are performed:
i) a step of applying a composition (A) or ($A_1$) comprising one or more compounds chosen from: (1'), (2'), (3'), (4') and (5');
then
ii) a switching-off step which consists in applying to said fibers a composition (C) at acidic pH;
then
iii) a revelation step which consists in applying to said fibers a composition
(B) at basic pH;
it being understood that steps ii) and iii) may be repeated several times.

The application of composition (A) or ($A_1$) of the process according to the invention may optionally be followed by rinsing.

The application of composition (B) of the process of the invention may also optionally be followed by rinsing.

The application of composition (C) of the process of the invention may also optionally be followed by rinsing.

Preferably, the application of composition (A) or ($A_1$) of the process according to the invention is followed by drying, preferably after rinsing.

The application of composition (B) of the process of the invention may also optionally be followed by drying.

The application of composition (C) of the process of the invention may also optionally be followed by drying.

The drying step may be performed either in the air (natural drying) or with any heating device such as a hairdryer or heating lamps or a heating hood, optionally in combination with straightening with a brush (blow drying), takes place before the straightening step using a straightening iron.

Composition (A) or ($A_1$) of the invention may be applied to dry or wet keratin fibers, preferably to dry or wet hair, preferably to dry hair.

The bath ratio of composition (A) or ($A_1$) applied may range from 0.1 to 20, more particularly from 0.2 to 15, preferably between 0.5 and 13, even more preferentially from 1 to 12. The term "bath ratio" means the ratio between the total weight of the applied composition and the total weight of keratin materials to be treated.

The leave-on time of composition (A) or ($A_1$) of the invention is preferably between 3 and 120 minutes, preferably between 5 and 60 minutes and even more preferentially between 10 and 40 minutes, such as 30 minutes.

The application temperature is generally set at between room temperature and 80° C., preferably between 25 and 55° C. and more particularly between 28 and 40° C.

A Device or Kit

Another subject of the invention is a multi-compartment device or kit which comprises, i) in a first compartment: the triarylmethane or sulfonophthalein compounds of formula (I) or (I') as defined previously and optionally one or more halochromic additional dyes other than the triarylmethanes as defined previously, ii) in a second compartment: a composition (B) at basic pH as defined previously; and iii) in a third compartment: a composition (C) at acidic pH as defined previously.

Preferably, the multi-compartment kit of the invention comprises, i) in a first compartment: a composition (A) or ($A_1$) as defined previously, ii) in a second compartment: a composition (B) at basic pH; and iii) in a third compartment: a composition (C) at acidic pH.

Another subject of the invention is a composition ($A_1$) comprising:

one or more compounds of formula (I) or (I') as defined previously;

optionally one or more additional dyes as defined previously;

one or more hydrotropic solvents as defined previously and optionally one or more additional solvents other than the hydrotropic solvents as defined previously; and/or one or more thickeners, particularly polymeric thickeners, as defined previously.

The examples that follow serve to illustrate the invention without, however, being limiting in nature.

EXAMPLES

Example 1

The following compositions were prepared; the amounts are given in g per 100 g of composition:

Composition (A') comprising the compounds of formula (I) of the invention and comparative composition (A") comprising the triarylmethane dye outside the invention; the amounts are given in g per 100 g of composition

| Ingredients | Composition (A') invention | Comparative composition (A") |
|---|---|---|
| Ethanol | 15 | 15 |
| Hydroxyethylcellulose (HEC-Natrosol 250 HHR) | 1.5 | 1.5 |
| Benzyl alcohol | 5 | 5 |
| Phenoxyethanol | 1 | 1 |
| Caprylyl glycol | 1 | 1 |
| Sodium salt of Chlorophenol Red (1') | 0.5 | — |
| Disodium salt of Erioglaucine | — | 0.5 |
| Water | qs 100 | qs 100 |

"Switch-on" revealing composition (B') at basic pH

| Ingredients | Amount |
|---|---|
| Monoethanolamine (MEA) | 5 |
| Water | qs 100 | pH of the composition 11.4±0.5

"Switch-off" erasing composition (C') at acidic pH:

| Ingredients | Amount |
|---|---|
| Phosphoric acid | 5 |
| Water | qs 100 | pH of the composition 1.4±0.5

Each of the compositions (A') according to the invention and comparative compositions (A") are applied to locks according to the same protocol, namely:

a lock of natural hair containing 90% white hairs (tone depth TD9)

then left to stand on the lock for 30 minutes at 31° C.

then rinsing with water, then drying

Once the keratin fibers have been dried, the "switch" treatment is applied.

To obtain "switching on", composition (B') is applied to each lock by spraying.

To obtain "switching off", composition (C') is applied to each lock by spraying.

Colorimetric Results:

The color of the locks was evaluated in the CIE L* a* b* system, using a ColorShot MultiSpectral colorimeter (illuminant D65, angle 10°). In this L* a* b* system, the three parameters respectively denote the intensity of the color (L*), the green/red color axis (a*) and the blue/yellow color axis (b*). The lower the value of L*, the more intense the color.

Color Build-Up:

The colorimetric measurements were taken just after applying composition (A') or (A"), and then after each of the "switch" treatments.

The variation in coloring between the locks of untreated hair and of treated hair is defined by ($\Delta E^*$) according to the following equation:

$$\Delta E^* = \sqrt{(L^*-L_0^*)^2 + (a^*-a_0^*)^2 + (b^*-b_0^*)^2}$$

In this equation, L*, a* and b* represent the values measured on locks of hair after treatment and $L_0^*$, $a_0^*$ and $b_0^*$ represent the values measured on locks of hair before treatment. The higher the value of $\Delta E^*$, the greater the color build-up.

The variation in coloring between the locks of hair treated and revealed (switched on) with composition (B) and erased (switched off) with composition (C) is defined by ($\Delta E^*_{ON-OFF}$) according to the following equation:

$$\Delta E^*_{ON-OFF} = \sqrt{(L^*_{OFF} - L^*_{ON})^2 + (a^*_{OFF} - a^*_{ON})^2 + (b^*_{OFF} - b^*_{ON})^2}$$

In this equation, $L^*_{ON}$, $a^*_{ON}$ and $b^*_{ON}$ represent the values measured on locks of hair after treatment with composition (A') or (A") and then application of the revealing composition (B) and $L^*_{OFF}$, $a^*_{OFF}$ and $b^*_{OFF}$ represent the values measured on locks of hair after treatment with composition (A') or (A"), then application of the revealing composition (B') and then application of the erasing composition (C'). The higher the value of $\Delta E^*_{ON-OFF}$, the greater the variation in color between the application of the revealer and of the eraser.

| Name | Treatment | L* | a* | b* | C | ΔE vs reference | ΔE switch on vs. SWITCH OFF |
|---|---|---|---|---|---|---|---|
| Composition (A') of the invention | Spontaneous result* | 36.4 | 5.5 | 16.4 | 17.4 | 18.8 | |
| Composition (A') of the invention | SWITCH ON | 30.8 | 9.8 | 3.3 | 10.4 | 31.1 | 35.8 |
| Composition (A') of the invention | SWITCH OFF | 46.5 | 18.4 | 34.4 | 39.0 | 13.9 | |
| Comparative Composition (A") | Spontaneous result* | 44.1 | −15.2 | 9.6 | 18.0 | 30.4 | |
| Comparative Composition (A") | SWITCH ON | 44.4 | −13.6 | 11.1 | 17.6 | 28.2 | 1.8 |
| Comparative Composition (A") | SWITCH OFF | 46.1 | −13.2 | 11.4 | 17.5 | 27.3 | |

It is seen from the results in the above table that after composition (A') of the invention has been applied before the switch treatment, the composition of the invention makes it possible to obtain significantly more intense coloring than that of the comparative composition (36.4 versus 44.1). On applying the revealer (composition B') to the keratin fibers treated with composition (A') of the invention, the color becomes much more intense (30.8 versus 36.4), whereas for the fibers treated with the comparative composition (A"), the intensity virtually does not change (44.4 versus 44.1). Next, on applying the erasing composition (C) to the keratin fibers treated with composition (A') of the invention, the color lightens very significantly ($\Delta L^*_{ON-OFF}$=46.5-30.8=15.7), whereas for the fibers treated with the comparative composition, the lightening is very weak ($\Delta L^*_{ON-OFF}$=46.1-44.4=1.7).

Moreover, as regards the color build-up, a very large amplitude was measured for the colors obtained via the process of the invention, namely after applying composition (A'), the ΔE* of color build-up is ΔE*=18.8, after application of the revealing composition (B'), ΔE*=31.1; and after application of the erasing composition (C'), ΔE=13.9. In addition, the value of $\Delta E^*_{ON-OFF}$ for the process of the invention is $\Delta E^*_{ON-OFF}$=35.8. For the comparative process, the values obtained are, respectively, after applying composition (A'), ΔE*=30.4, after applying composition (B'), ΔE*=28.2 and after applying composition (C'), ΔE*=27.3 with a value for $\Delta E^*_{ON-OFF}$=1.8.

It is thus seen that the "switch on-switch off" revealed-erased coloring amplitude is much larger via the process of the invention compared with that of the comparative process.

In addition, the process according to the invention allows successive appearance(s)/disappearance(s) of color within a few seconds, generally on applying the revealing composition, without the need to use a hairdryer. Numerous ON/OFF cycles may be performed in sequence, and very good persistence of the order of 5 to 8 shampoo washes was observed. Moreover, the integrity and feel of the hair are respected.

Other dyes according to the invention were evaluated as regards the intensity and the variation $\Delta E^*_{ON-OFF}$ on light-colored hair and on dark hair.

Results on light-colored hair (tone depth=10):

| Compound | Treatment | Shade | L* | a* | b* | $\Delta E^*_{ON-OFF}$ |
|---|---|---|---|---|---|---|
| Chlorophenol Red (1') | OFF | Yellow | 61.5 | 24.7 | 58.7 | 86.6 |
| | ON | Violet | 32.7 | 25.9 | −23.0 | |
| Bromocresol Purple (2) | OFF | Yellow | 66.7 | 17.9 | 63.2 | 95.7 |
| | ON | Blue | 31.6 | 13.8 | −25.7 | |
| Bromocresol Purple Na Salt, (2') | OFF | Yellow | 66.1 | 15.0 | 62.1 | 89.8 |
| | ON | Blue | 31.2 | 10.8 | −20.5 | |
| Bromothymol Blue Na Salt, (3') | OFF | Yellow | 66.5 | 20.1 | 59.4 | 84.1 |
| | ON | Blue | 36.3 | −10.4 | −12.9 | |
| Bromocresol Green (4) | OFF | Yellow | 53.8 | 16.2 | 40.5 | 60.5 |
| | ON | Blue | 35.7 | −12.5 | −9.6 | |
| Phenol Red (5) | OFF | Yellow | 64.4 | 32.6 | 54.8 | 61.5 |
| | ON | Red | 36.6 | 36.1 | 0.0 | |

It is seen from the above table that the process of the invention using the compounds of formula (I) or (I') makes it possible to obtain significantly stronger intensities (L* significantly smaller between the colors after application of the revealer (switch on) than after application of the erasing composition (switch off)). Furthermore, the color variations $\Delta E^*_{ON-OFF}$ between the switch-off treatment and the switch-on treatment are very high (>60). This tendency was observed even after several switch-off-switch-on cycles.

Results on dark hair (TD=4):

| Name | Treatment on dark hair TD4 | L* | a* | b* | C | ΔE vs reference | ΔE switch on vs. SWITCH OFF |
|---|---|---|---|---|---|---|---|
| Chlorophenol Red (1') | ON | 23.7 | 3.6 | 6.1 | 7.1 | 31.1 | 4.8 |
| Chlorophenol Red (1') | OFF | 21.7 | 3.2 | 1.8 | 3.7 | 13.9 | |
| Bromocresol Purple Na Salt (2') | ON | 24.3 | 3.2 | 6.2 | 7.0 | 24.3 | 5.1 |
| Bromocresol Purple Na Salt (2') | OFF | 21.5 | 2.0 | 2.2 | 3.0 | 21.5 | |
| Bromocresol Green (4) | ON | 24.0 | 2.7 | 5.3 | 6.0 | 24.0 | 4.1 |
| Bromocresol Green (4) | OFF | 21.8 | 0.5 | 2.8 | 2.8 | 21.8 | |

| Compound | Treatment | Shade |
|---|---|---|
| Chlorophenol Red (1') | OFF | Yellow |
| | ON | Violet |
| Bromocresol Purple Na Salt (2') | OFF | Yellow |
| | ON | Blue |
| Bromocresol Green (4) | OFF | Yellow |
| | ON | Blue |

It is seen from the above table that the process of the invention using the compounds of formula (I) or (I') makes it possible to obtain significantly stronger intensities and chromaticity observable even on dark hair (L* and C* significantly smaller between the colors after application of the revealer (switch on) than after application of the erasing composition (switch off)).

Example 2: Comparative Study (Vs. FR 1 441 822)

The following compositions were prepared:

| Ingredients | Composition (A$_2$) Invention | Composition P Comparative |
|---|---|---|
| Bromothymol Blue Na Salt (3') | 1.55 × 10$^{-3}$ mol | |
| Alizarin red | | 1.55 × 10$^{-3}$ mol |
| EtOH/Water 50/50 wt | qs 100 g | qs 100 g |

"Switch-on" revealing composition (B$_1$) at basic pH

| Ingredients | Amount |
|---|---|
| Monoethanolamine (MEA) | 5 g |
| Water | qs 100 g | pH of the composition 11.4±0.5

"Switch-off" erasing composition (C$_1$) at acidic pH:

| Ingredients | Amount |
|---|---|
| Phosphoric acid | 5 g |
| Water | qs 100 g | pH of the composition 1.3±0.5

Each of the compositions (A$_2$) and (P) are applied to locks (1.5 g of composition/g of hair) according to the same protocol, namely:
- a lock of natural hair containing 90% white hairs
- then left to stand on the lock for 30 minutes at 31° C.
- then rinsing with water, then drying Once the keratin fibers have been dried, the "switch" treatment is applied.
- To obtain "switching on", composition (B$_1$) is applied to each lock by spraying.
- To obtain "switching off", composition (C$_1$) is applied to each lock by spraying.

Colorimetric Results:

The color of the locks was evaluated in the CIE L* a* b* system, using a Konica-Minolta 3600d colorimeter (illuminant D65, angle 10°).

The variation in coloring between the locks of hair treated and revealed (switched on) with composition (B$_1$) and erased (switched off) with composition (C$_1$) is defined by $\Delta E^*_{ON-OFF}$ as in example 1.

The higher the value of $\Delta E^*_{ON-OFF}$, the greater the variation in color between the application of the revealer and of the eraser.

| Nom | | L* | a* | b* | $\Delta E^*_{ON-OFF}$ |
|---|---|---|---|---|---|
| A$_2$ (Invention) | SWITCH OFF Acidic pH | 62.6 | 3.9 | 29.1 | 32.6 |
| | SWITCH ON Basic pH | 52.1 | −10.6 | 1.8 | |
| P (Comparative) | SWITCH OFF Acidic pH | 60.8 | 6.8 | 21.2 | 18 |
| | SWITCH ON Basic pH | 51.2 | 10.4 | 6.4 | |

It is thus seen that the "switch on-switch off" revealed-erased colouring amplitude is much larger via the process of the invention compared with that of the comparative process.

The invention claimed is:

1. A method for treating keratin fibers, wherein the method comprises:
   i) applying to the keratin fibers a composition (A) comprising at least one compound chosen from compounds of formula (I) or (I'), mineral or organic base salts thereof, optical isomers thereof, geometrical isomers thereof, or tautomeric isomers thereof, or solvates thereof:

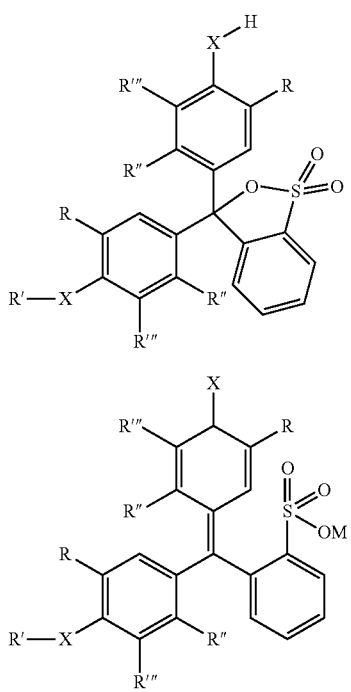

wherein in formulae (I) and (I'):
  R is chosen from a hydrogen atom, a halogen atom, a ($C_1$-$C_6$)alkyl a group, or a ($C_1$-$C_6$)alkoxy group;
  R' is chosen from a hydrogen atom, a ($C_1$-$C_6$)alkyl group, or a benzyl group;
  R" is chosen from a hydrogen atom, a ($C_1$-$C_6$)alkyl group, or a ($C_1$-$C_6$)alkoxy groups;
  R''' is chosen from a hydrogen atom, a halogen atom, or a group chosen from hydroxyl, ($C_1$-$C_4$)alkyl, ($C_1$-$C_6$)alkoxy, or carboxyl groups;
  X is chosen from a heteroatom; and
  M is chosen from a hydrogen atom, an alkali metal, an alkaline-earth metal, or an ammonium group;
ii) applying to the keratin fibers a composition (B) having a basic pH to switch on a change of a color of the keratin fibers; and
iii) applying to the keratin fibers a composition (C) having an acidic pH to switch off the change of the color of the keratin fibers;
wherein:
when the composition (A) comprises at least one compound chosen from compounds of formula (I), the applying the composition (A) is followed by ii) applying the composition (B), and the applying the composition (B) is followed by iii) applying of the composition (C);
when the first composition (A) comprises at least on compound chosen from compounds of formula (I'), the applying the composition (A) is followed by iii) applying the composition (C), and the applying the composition (C) is followed by ii) the applying the composition (B); and
wherein steps ii) and iii) are optionally repeated several times.

2. The method of claim 1, wherein the at least one compound chosen from compound of formula (I) or (I') is a dye with a color change zone at a pH ranging from 4.5 to 8.

3. The method of claim 1, wherein the at least one compound of formula (I) or (I') is chosen from compounds of formula (Ia), (I'a), (Ib), (I'b), (Ic), (I'c), (Ie). (I'e), (If), or (I'f), or the alkali metal or alkaline-earth metal salts thereof:

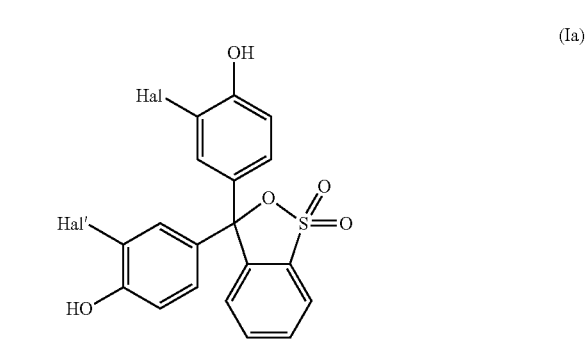

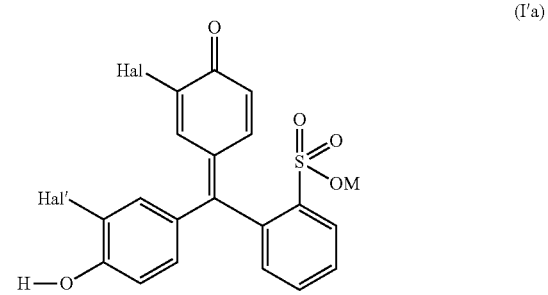

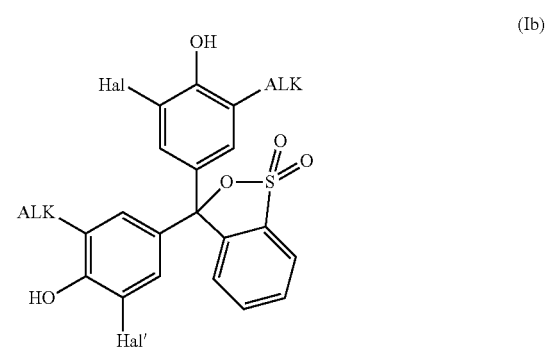

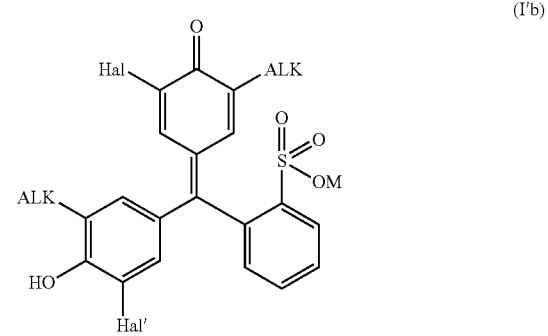

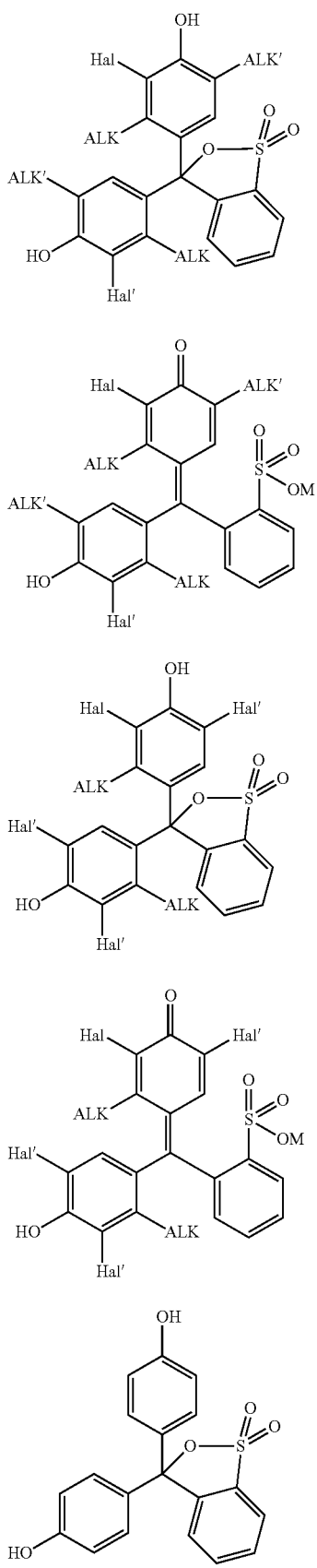

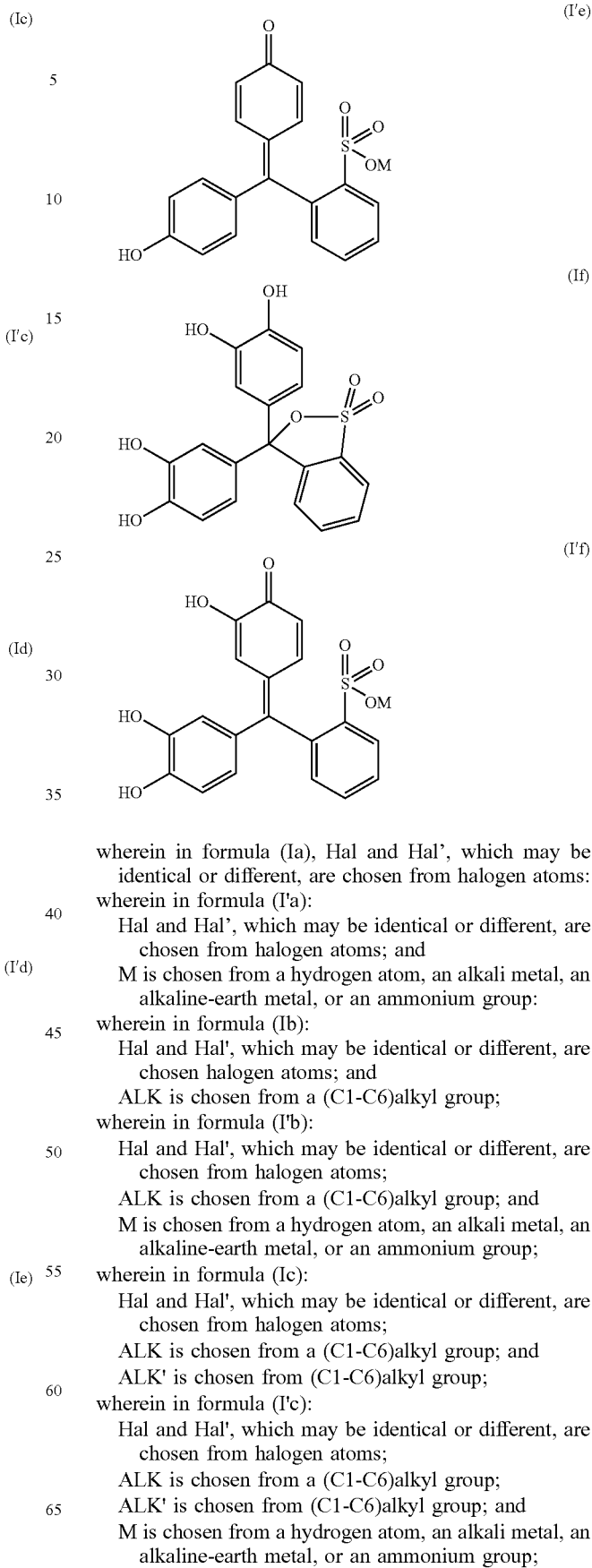

wherein in formula (Ia), Hal and Hal', which may be identical or different, are chosen from halogen atoms:
wherein in formula (I'a):
  Hal and Hal', which may be identical or different, are chosen from halogen atoms; and
  M is chosen from a hydrogen atom, an alkali metal, an alkaline-earth metal, or an ammonium group:
wherein in formula (Ib):
  Hal and Hal', which may be identical or different, are chosen halogen atoms; and
  ALK is chosen from a (C1-C6)alkyl group;
wherein in formula (I'b):
  Hal and Hal', which may be identical or different, are chosen from halogen atoms;
  ALK is chosen from a (C1-C6)alkyl group; and
  M is chosen from a hydrogen atom, an alkali metal, an alkaline-earth metal, or an ammonium group;
wherein in formula (Ic):
  Hal and Hal', which may be identical or different, are chosen from halogen atoms;
  ALK is chosen from a (C1-C6)alkyl group; and
  ALK' is chosen from (C1-C6)alkyl group;
wherein in formula (I'c):
  Hal and Hal', which may be identical or different, are chosen from halogen atoms;
  ALK is chosen from a (C1-C6)alkyl group;
  ALK' is chosen from (C1-C6)alkyl group; and
  M is chosen from a hydrogen atom, an alkali metal, an alkaline-earth metal, or an ammonium group;

wherein in formula (Id):
  Hal and Hal', which may be identical or different, are chosen from halogen atoms: and
  ALK is chosen from a (C$_1$-C$_6$) alkyl group;
wherein in formula (I'd):
  Hal and Hal', which may be identical or different, are chosen from halogen atoms;
  ALK is chosen from a (C1-C6)alkyl group; and
  M is chosen from a hydrogen atom, an alkali metal, an alkaline-earth metal, or an ammonium group;
wherein in formula (I'e): M is chosen from a hydrogen atom, an alkali metal, an alkaline-earth metal, or an ammonium group; and
wherein in formula (I'f): M is chosen from a hydrogen atom, an alkali metal, an alkaline-earth metal, or an ammonium group.

4. The method of claim 1, wherein the at least one compound of formula (I) or (I') is chosen from compounds of formula (1), (1'), (2), (2'), (3), (3'), (4), (4'), (5), (5'), (6), or (6') below:

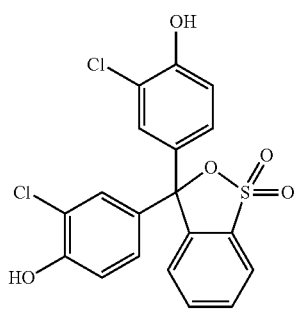
(1)

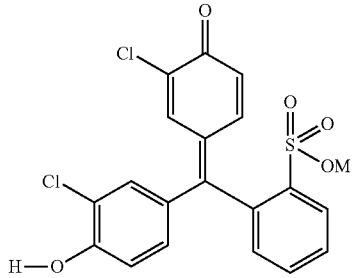
(1')

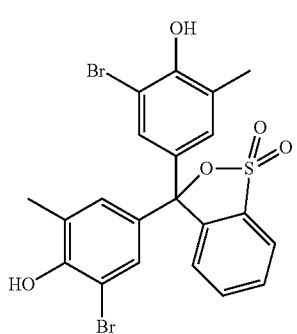
(2)

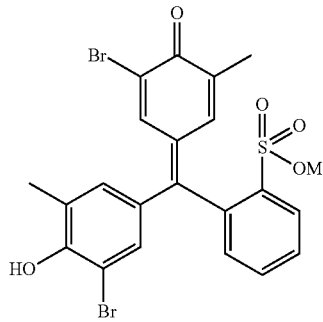
(2')

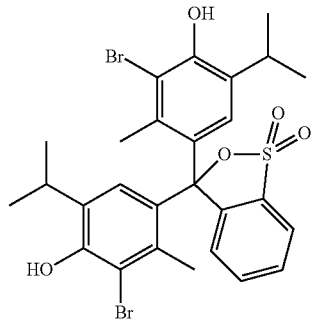
(3)

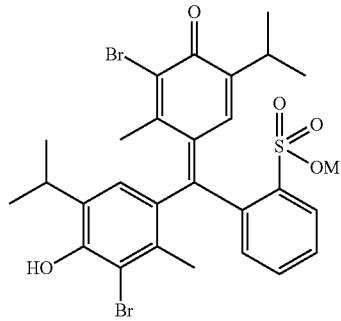
(3')

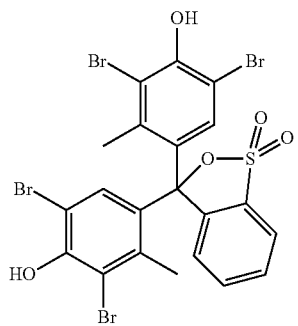
(4)

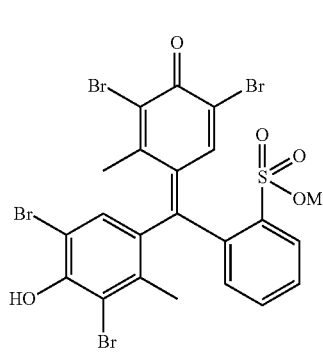
(4')

-continued (5)
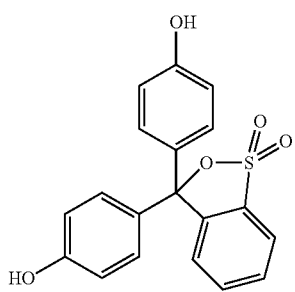

(5')
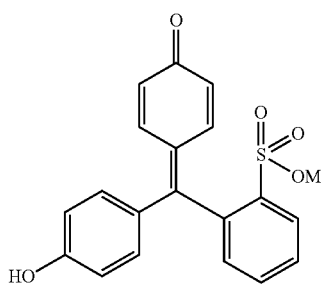

(6)
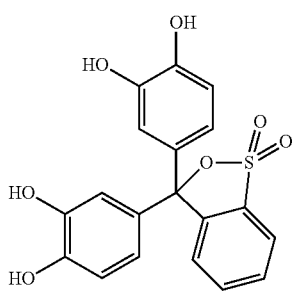

(6')
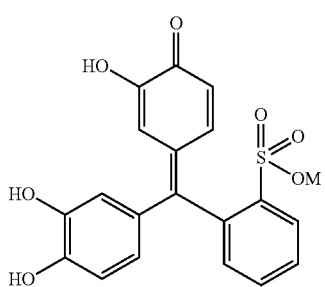

wherein in formulae (1'), (2'), (3'), (4'), (5'), and (6'), M is chosen from a hydrogen atom, an alkali metal, an alkaline-earth metal, or an ammonium group.

5. The method of claim 1, wherein the at least one compounds of formula (I) or (I') is present in an amount ranging from 0.001% to 10% by weight, relative to the total weight of composition (A).

6. The method of claim 1, wherein the composition (A) further comprises at least one additional halochromic dye other than the at least one compound of formula (I) or (I'), and the at least one additional halchromic dye is chosen from compounds of formulae (II) or (II'), mineral or organic base salts thereof, optical isomers thereof, geometrical isomers thereof. tautomeric isomers thereof, or solvates thereof:

(II)
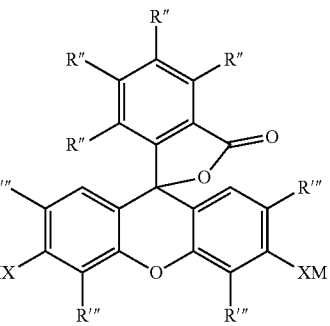

(II')
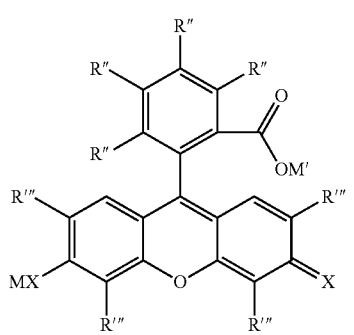

wherein in formulae (II) and (II'):

R" is chosen from a hydrogen atom, a halogen atom, or a group chosen from i) $(C_1-C_6)$alkyl which is optionally substituted with at least one halogen atom, ii) optionally substituted $(C_1-C_6)$alkoxy, iii) $R_a$-C(X)-, iv) $R_a$-C(X)-X-, v) Ra-X- C(X)-, or vi) iso(thio)cyanate, with $R_a$ being chosen from a hydrogen atom, a heterocyclic group, a $(C_1-C_4)$alkyl group optionally substituted with at least one halogen atom, or at least one carboxyl groups;

R''' is chosen from i) a hydrogen atom, ii) a halogen atom or iii) a group chosen from $(C_1-C_6)$alkyl which is optionally substituted with at least one group chosen from: a) hydroxyl, b) (di)$(C_1-C_4)$(alkyl)amino, c) (di)carboxy$(C_1-C_4)$alkylamino, or iv) $(C_1-C_6)$alkoxy;

X is chosen from a heteroatom; and

M is chosen from a hydrogen atom, an alkali metal or alkaline-earth metal, an ammonium group, or a $(C_1-C_6)$alkyl(thio)carbonyl group; and M' is chosen from a hydrogen atom, an alkali metal, an alkaline-earth metal, or an ammonium group.

7. The method of claim 1, wherein the composition (A) further comprises at least one additional halochromic dye chosen from compounds of formula (IIa), (II'a), (IIb), (II'b), (IIc), (II'c), (IId), (II'd), (IIe), (II'e), (IIf), or (II'f):

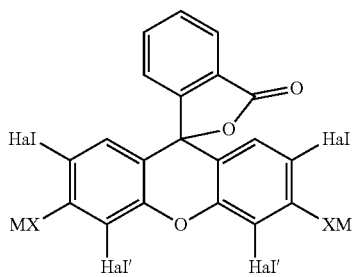

(IIa)

wherein in formula (IIa):
Hal and Hal', which may be identical or different, are chosen from halogen atoms;
X is chosen from a heteroatom: and
M is chosen from a hydrogen atom, an alkali metal or alkaline-earth metal, an ammonium group, or a ($C_1$-$C_6$)alkyl(thio)carbonyl group;

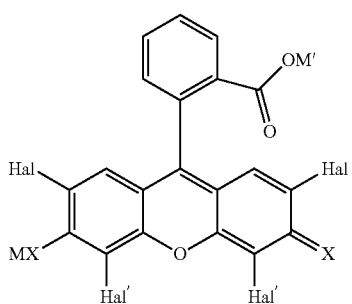

(II'a)

wherein in formula (II'a):
Hal and Hal', which may be identical or different, are chosen from halogen atoms;
X is chosen from a heteroatom;
M is chosen from a hydrogen atom, an alkali metal or alkaline-earth metal, an ammonium group, or a (C1-C6)alkyl(thio)carbonyl group; and
M' is chosen from a hydrogen atom, an alkali metal, an alkaline-earth metal, or an ammonium group:

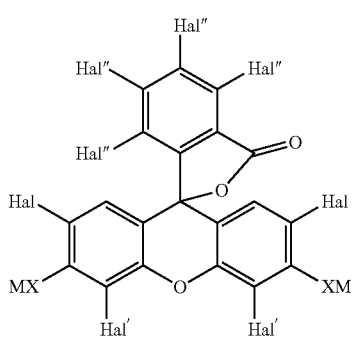

(IIb)

wherein in formula (IIb):
Hal, Hal', and Hal", which may be identical or different, are chosen from halogen atoms;
X is a heteroatom; and
M is chosen from a hydrogen atom, an alkali metal or alkaline-earth metal, an ammonium group, or a (C1-C6)alkyl(thio)carbonyl group;

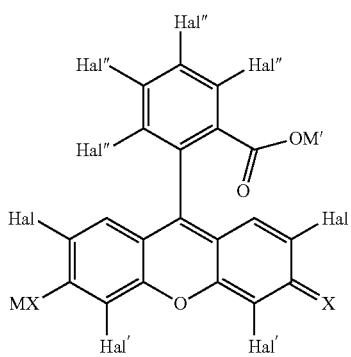

(II'b)

wherein in formula (II'b):
Hal, Hal', and Hal", which may be identical or different, are chosen from halogen atoms;
X is a heteroatom;
M is chosen from a hydrogen atom. an alkali metal or alkaline-earth metal, an ammonium group, ora (C1-C6)alkyl(thio)carbonyl group; and
M' is chosen from a hydrogen atom, an alkali metal, an alkaline-earth metal, or an ammonium group;

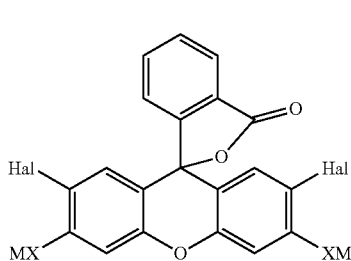

(IIc)

wherein in formula (IIc):
Hal is a halogen atom;
X is a heteroatom; and
M is chosen from a hydrogen atom, an alkali metal or alkaline-earth metal, an ammonium group, ora (C1-C6)alkyl(thio)carbonyl group;

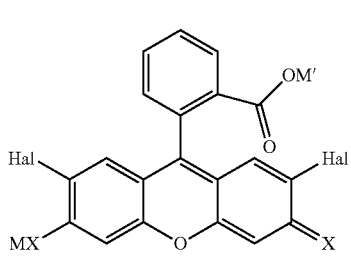

(II'c)

wherein in formula (II'c):
Hal is a halogen atom;
X is a heteroatom;
M is chosen from a hydrogen atom, an alkali metal or alkaline-earth metal, an ammonium group, or a (C1-C6)alkyl(thio)carbonyl group; and M' is chosen from a hydrogen atom, an alkali metal, an alkaline-earth metal, or an ammonium group;

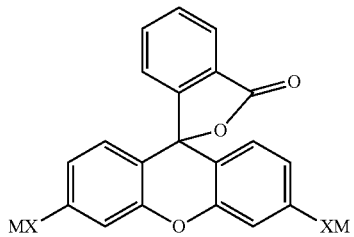
(IId)

wherein in formula (IId):
X is a heteroatom; and
M is chosen from a hydrogen atom, an alkali metal or alkaline-earth metal, an ammonium group, or a (C1-C6)alkyl(thio)carbonyl group;

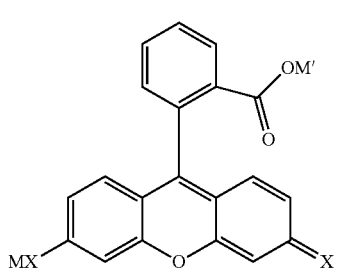
(II'd)

wherein in formula (II'd):
X is a heteroatom;
M is chosen from a hydrogen atom, an alkali metal or alkaline-earth metal, an ammonium group, or a (C1-C6)alkyl(thio)carbonyl group; and
M' is chosen from a hydrogen atom, an alkali metal, an alkaline-earth metal, or an ammonium group;

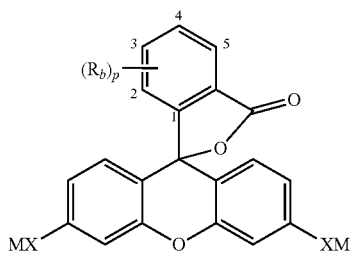
(IIe)

wherein in formula (IIe):
$R_b$ is chosen from i) optionally substituted $(C_1-C_4)$ alkyl, ii) isothiocyanate, iii) $R_a$-O-C(O)- or iv) $R_a$-C(O)-N(R')-, wherein $R_a$ is chosen from a hydrogen atom, a heterocyclic group, a $(C_1-C_4)$alkyl group, or at least one carboxyl groups optionally substituted with at least one halogen atom;
X is a heteroatom;
p is an integer between 1 and 5; and; and
M is chosen from a hydrogen atom, an alkali metal or alkaline-earth metal, an ammonium group, or a (C1-C6)alkyl(thio)carbonyl group;

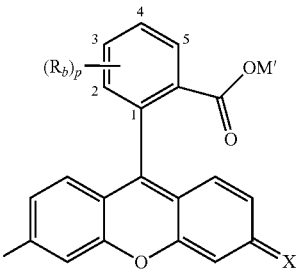
(II'e)

wherein in formula (II'e):
$R_b$ is chosen from i) optionally substituted $(C_1-C_4)$ alkyl, ii) isothiocyanate, iii) $R_a$-O-C(O)-, or iv) $R_a$-C(O)-N(R)- with $R_a$ chosen from a hydrogen atom, a heterocyclic group, a $(C_1-C_4)$alkyl group, or at least one carboxyl groups optionally substituted with at least one halogen atom;
X is a heteroatom;
p is an integer between 1 and 5; and ;
M is chosen from a hydrogen atom, an alkali metal or alkaline-earth metal, an ammonium group, ora (C1-C6)alkyl(thio)carbonyl group; and
M' is chosen from a hydrogen atom, an alkali metal, an alkaline-earth metal, or an ammonium group;

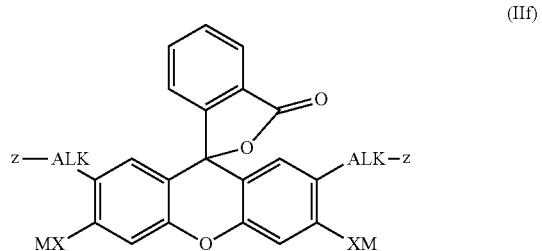
(IIf)

wherein in formula (IIf):
ALK is an $(C_1-C_4)$alkylene group;
Z is chosen from a group $NR_cR_d$ wherein Rc and Rd, which may be identical or different, are chosen from a hydrogen atom or a $(C_1-C_4)$alkyl group optionally substituted with at least one carboxyl group:
X is a heteroatom; and
M is chosen from a hydrogen atom, an alkali metal or alkaline-earth metal, an ammonium group, or a (C1-C6)alkyl(thio)carbonyl group;

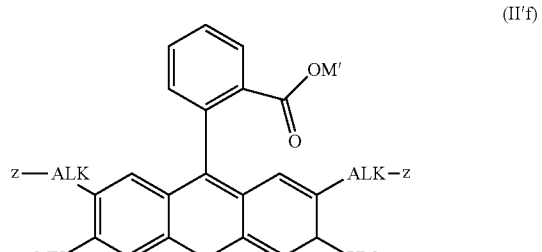
(II'f)

wherein in formula (II'f):

ALK is a $(C_1-C_4)$alkylene group;

Z is chosen from a group $NR_cR_d$, wherein Rc and Rd, which may be identical or different, are chosen from a hydrogen atom or a $(C_1-C_4)$alkyl group optionally substituted with at least one carboxyl group:

X is a heteroatom;

M is chosen from a hydrogen atom, an alkali metal or alkaline-earth metal, an ammonium group, or a (C1-C6)alkyl(thio)carbonyl group; and M' is chosen from a hydrogen atom, an alkali metal, an alkaline-earth metal, or an ammonium group.

8. The method of claim 6, wherein the at least one additional halochromic dye is chosen from compounds of formula 1, 1', 2, 2', 3, 3', 4, 4', 5, 5', 6, or 6':

1

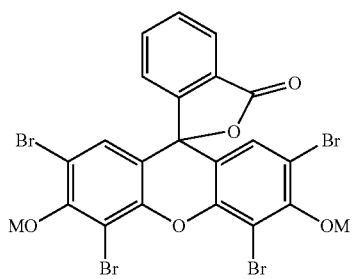

1'

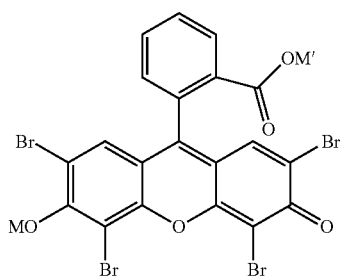

2

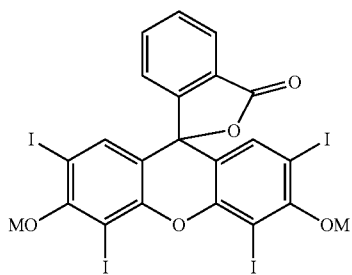

2'

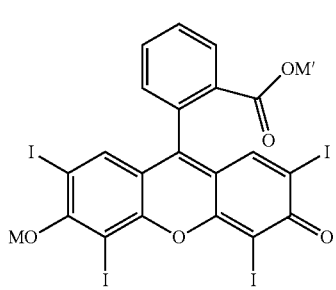

3

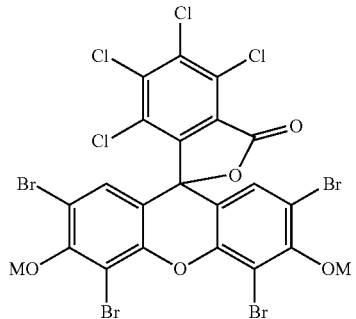

3'

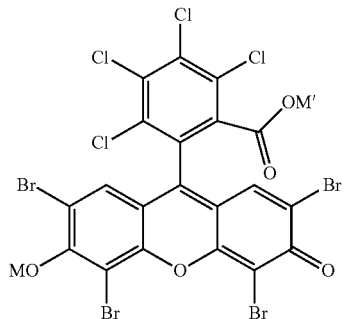

4

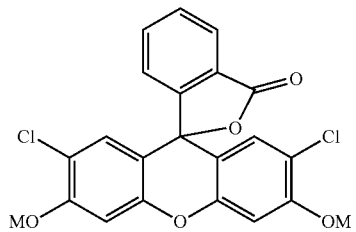

4'

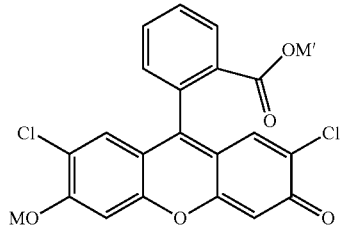

5

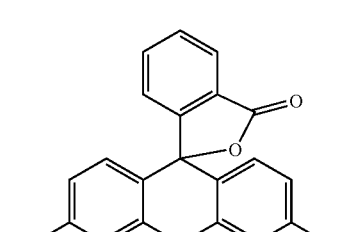

5'

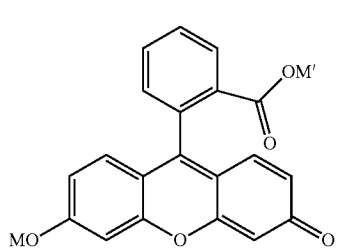

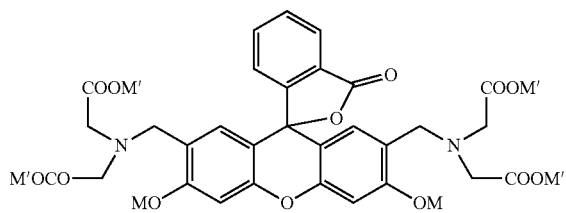

6

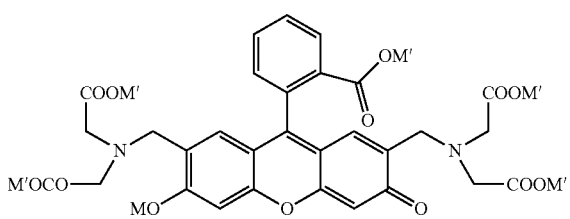

6' wherein in formulae 1, 1', 2, 2', 3, 3', 4, 4', 5, 5', 6, and 6',
M is chosen from a hydrogen atom, an alkali metal or alkaline-earth metal, an ammonium group, or a (C1-C6)alkyl(thio)carbonyl group; and
M' is chosen from a hydrogen atom, an alkali metal, an alkaline-earth metal, or an ammonium group.

9. The method of claim 6, wherein the at least one halochromic dye other than the at least one compound of formula (I) or (I') is present in an amount ranging from 0.001% to 10% by weight, relative to the total weight of the composition (A).

10. The method of claim 1, wherein the composition (B) has a pH ranging from 7.5 to 12.5.

11. The method of claim 1, wherein the composition (B) comprises at least one mineral or organic alkaline agent chosen from:
a) aqueous ammonia,
b) alkanolamines,
c) oxyethylenated and/or oxypropylenated $(C_1-C_6)$alkylenediamines,
d) mineral or organic hydroxides,
e) basic amino acids.
f) alkali metal or alkaline-earth metal silicates or metasilicates,
g) carbonates and bicarbonates, or
h) compounds of formula (III) below:

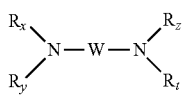

(III)

wherein in formula (III), W is a divalent $C_1-C_6$ alkylene radical optionally substituted with a hydroxyl group or a $C_1-C_6$ alkyl radical; $R_x$, $R_y$, $R_z$ and $R_t$, which may be identical or different, are chosen from a hydrogen atom, or a $C_1-C_6$alkyl group, a $C_1-C_6$ hydroxyalkyl group, or a $C_1-C_6$ aminoalkyl group.

12. The method of claim 1, wherein the composition (C) has a pH ranging from 0.5 to 6.

13. The method of claim 1, wherein the composition (C) comprises at least one organic or mineral acid chosen from i) hydrochloric acid HCl, ii) hydrobromic acid HBr, iii) sulfuric acid $H_2SO_4$, iv) phosphoric or orthophosphoric acid $H_3PO_4$, v) $(C_1-C_6)$alkylsulfonic acids (Alk-S(O)$_2$OH); vi) arylsulfonic acids (Ar-S(O)$_2$OH); vii) carboxylic acids; viii) sulfonic acids: ix) $(C_1-C_6)$alkoxysulfinic acids (Alk-O-S(O)OH); x) aryloxysulfinic acids: xi) triflic acid $CF_3SO_3H$; or xii) tetrafluoroboric acid $HBF_4$.

14. The method of claim 1, wherein the composition (A) further comprises at least one hydrotropic solvent comprising at least one liquid organic compound with a Hansen solubility parameter δH of greater than 0 and less than 16 $MPa^{1/2}$.

15. The method of claim 1, wherein the composition (A) comprises at least one hydrotropic solvent chosen from:
alcohol ethers;
aliphatic esters of $C_1-C_4$ carboxylic acids and of $C_3-C_{10}$ monoalcohols or polyhydroxylated alcohols, interrupted with at least one non-adjacent ether function;
aromatic ethers;
$(C_6-C_{10})$aryl$(C_1-C_6)$alkyl ethers of a $C_1-C_6$ alkyl optionally bearing a hydroxyl group;
alkanols bearing an aryl substituent;
lactones of formula (iii), or mixtures thereof:

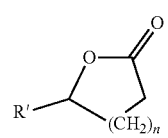

(iii)

wherein in formula (iii), R' is chosen from a hydrogen, a linear or branched $C_1-C_8$ alkyl, or a linear or branched $C_1-C_4$ hydroxyalkyl; n has the value of 1, 2 or 3; or
sulfones.

16. The method of claim 15,
wherein the alkanols bearing an aryl substituent comprise a $C_6-C_{10}$ aryl part and a $C_1-C_4$ alkyl part, wherein the alkyl part is terminated or interrupted with a heteroatom or a hydroxyl group; and
wherein the sulfones comprise at least one 5- to 7-membered cyclic sulfone optionally substituted with at least one $(C_1-C_4)$alkyl group, or mixtures thereof.

17. The method of claim 14, wherein the composition (A) further comprises at least one additional organic solvent other than the hydrotropic solvents, wherein the additional solvent is chosen from $C_1-C_4$ lower alkanols, polyols, or polyol ethers.

18. The method of claim 1 further comprising: after applying the composition (A) and before applying the composition (B) and/or the composition (C), drying the keratin fibers.

19. A composition $(A_1)$ comprising:
at least one dyeing compound chosen from compounds of formula (I) or (I'), mineral or organic base salts thereof, optical isomers thereof, geometrical isomers thereof, tautomeric isomers thereof, or solvates thereof:

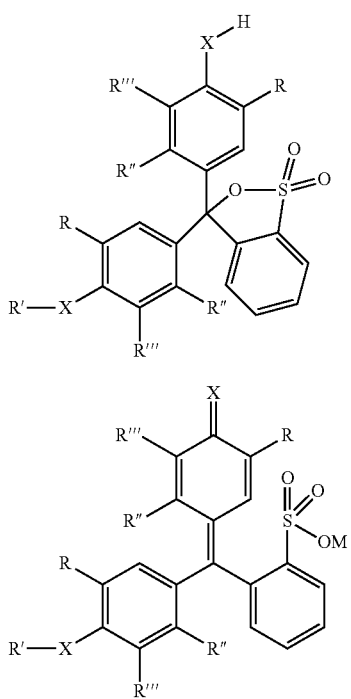

optionally at least one additional dye other than the at least one dyeing compound of formula (I) or (I), wherein the additional dye is chosen from compounds of formula (II) or (II'), mineral or organic base salts thereof, optical isomers thereof, geometrical isomers thereof, tautomeric isomers thereof, or solvates thereof:

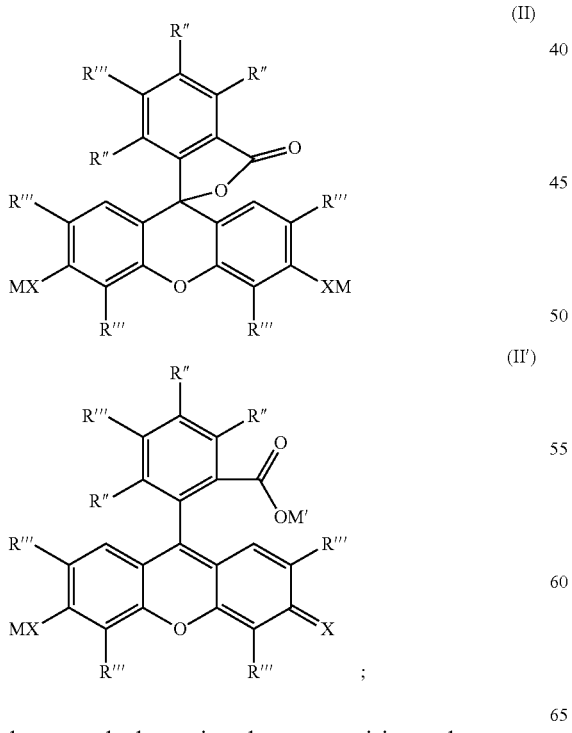

at least one hydrotropic solvent comprising at least one liquid organic compound with a Hansen solubility parameter δH of greater than 0 and less than 16 MPa$^{1/2}$, and optionally, at least one additional solvent other than the hydrotropic solvent chosen from $C_1$-$C_4$ lower alkanols, polyols, or polyol ethers; and/or at least one thickener;

wherein in formulae (I) and (I'):

R is chosen from a hydrogen atom, a halogen atom, a ($C_1$-$C_6$)alkyl group, or a ($C_1$-$C_6$)alkoxy group;

R' is chosen from a hydrogen atom, a ($C_1$-$C_6$)alkyl group, or a benzyl group;

R" is chosen from a hydrogen atom, a (C1-C6)alkyl group, or a (C1-C6)alkoxy group;

R''' is chosen from a hydrogen atom, a halogen atom, or a group chosen from hydroxyl, (C1-C4)alkyl, (C1-C6)alkoxy, or carboxyl groups;

X is a heteroatom; and

M is chosen from a hydrogen atom, an alkali metal, an alkaline-earth metal, or an ammonium group;

wherein the compounds of formula (I) do not comprise a compound in which X is an oxygen, R and R''' are bromine, and R' and R" are hydrogen atoms;

wherein in formulae (II) and (II'):

R" is chosen from a hydrogen atom, a halogen atom, or a group chosen from i) (C1-C6)alkyl which is optionally substituted, with at least one halogen atom, ii) optionally substituted (C1-C6)alkoxy, iii) Ra-C(X)-, iv) Ra-C(X)-X-, v) Ra-X-C(X)-, or vi) iso(thio)cyanate, wherein Ra is chosen from a hydrogen atom, a heterocyclic group, a (C1-C4)alkyl group optionally substituted with at least one halogen atom, or at least one carboxyl group;

R''' is chosen from i) a hydrogen atom, ii) a halogen atom, or iii) a group chosen from (C1-C6)alkyl, which is optionally substituted with at least one group chosen from: a) hydroxyl, b) (di)(C1-C4)(alkyl)amino, c) (di)carboxy(C1-C4)alkylamino. or iv) (C1-C6)alkoxy;

X is a heteroatom;

M is chosen from a hydrogen atom, an alkali metal or alkaline-earth metal, an ammonium group, or a (C1-C6)alkyl(thio)carbonyl group; and M' is chosen from a hydrogen atom, an alkali metal, an alkaline-earth metal, or an ammonium group.

20. A multi-compartment device comprising:

i) a first compartment comprising a composition (A) comprising at least one dyeing compound chosen from compounds of formula (I) or (I'), mineral or organic base salts thereof, optical isomers thereof, geometrical isomers thereof, or tautomeric isomers thereof, or solvates thereof:

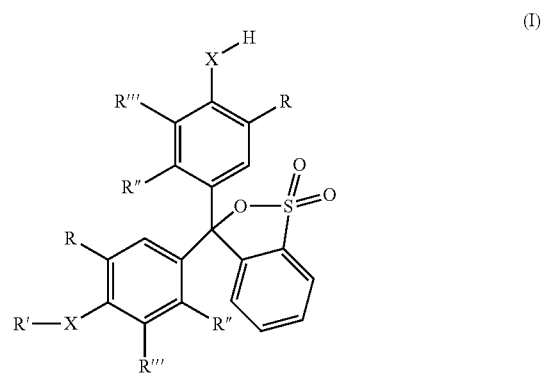

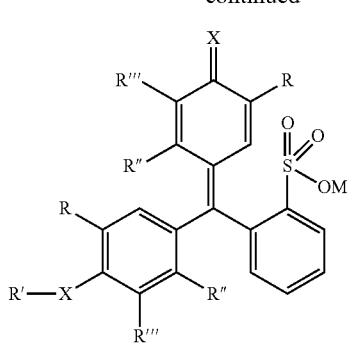

(I')

ii) a second compartment comprising a composition (B) at a basic pH comprising at least one mineral or organic alkaline agent; and iii) a third compartment containing a composition (C) at an acidic pH comprising at least one organic or mineral acid;

wherein in formulae (I) and (I'):

R is chosen from a hydrogen atom, a halogen atom, a $(C_1-C_6)$alkyl group, or a $(C_1-C_6)$alkoxy group:

R' is chosen from a hydrogen atom, a $(C_1-C_6)$alkyl group, or a benzyl group;

R'' is chosen from a hydrogen atom, a (C1-C6)alkyl group, or a (C1-C6)alkoxy group;

R''' is chosen from a hydrogen atom, a halogen atom, or a group chosen from hydroxyl, (C1-C4)alkyl, (C1-C6)alkoxy, or carboxyl groups;

X is a heteroatom; and

M is chosen from a hydrogen atom, an alkali metal, an alkaline-earth metal, or an ammonium group.

* * * * *

UNITED STATES PATENT AND TRADEMARK OFFICE
CERTIFICATE OF CORRECTION

| | | |
|---|---|---|
| PATENT NO. | : 11,273,112 B2 | Page 1 of 1 |
| APPLICATION NO. | : 16/955027 | |
| DATED | : March 15, 2022 | |
| INVENTOR(S) | : Arnaud Bonnamy et al. | |

It is certified that error appears in the above-identified patent and that said Letters Patent is hereby corrected as shown below:

In the Claims

Column 45, Claim 1, Line 37, please change "groups" to -- group --.

Column 45, Claim 1, Line 59, after "least" please change "on" to -- one --.

Column 54, Claim 7, Line 25, please change "ora" to -- or a --.

Column 54, Claim 7, Line 47, please change "ora" to -- or a --.

Column 55, Claim 7, Line 64, please delete the second "and".

Signed and Sealed this
Seventh Day of June, 2022

Katherine Kelly Vidal
*Director of the United States Patent and Trademark Office*